United States Patent
McNaughton et al.

(10) Patent No.: US 12,090,514 B2
(45) Date of Patent: *Sep. 17, 2024

(54) SYSTEM AND METHOD FOR BUOYANT PARTICLE PROCESSING

(71) Applicant: Akadeum Life Sciences, Inc., Ann Arbor, MI (US)

(72) Inventors: Brandon H. McNaughton, Ann Arbor, MI (US); Nadia Petlakh, Ann Arbor, MI (US); John G. Younger, Ann Arbor, MI (US); Greg Hermanson, Ann Arbor, MI (US); Bill Hyun, Ann Arbor, MI (US); Vanessa Kelchner, Ann Arbor, MI (US)

(73) Assignee: Akadeum Life Sciences, Inc., Ann Arbor, MI (US)

( * ) Notice: Subject to any disclaimer, the term of this patent is extended or adjusted under 35 U.S.C. 154(b) by 4 days.

This patent is subject to a terminal disclaimer.

(21) Appl. No.: 18/096,769

(22) Filed: Jan. 13, 2023

(65) Prior Publication Data
US 2023/0166291 A1 Jun. 1, 2023

Related U.S. Application Data

(63) Continuation of application No. 17/679,688, filed on Feb. 24, 2022, now Pat. No. 11,583,893, which is a
(Continued)

(51) Int. Cl.
*B05D 7/00* (2006.01)
*B05C 3/02* (2006.01)
(Continued)

(52) U.S. Cl.
CPC .............. *B05D 7/5883* (2013.01); *B05C 3/02* (2013.01); *B05C 11/10* (2013.01); *B05C 19/02* (2013.01);
(Continued)

(58) Field of Classification Search
CPC .......... B05D 7/5883; B05D 1/18; B05D 1/22; B05D 1/36; B05D 5/04; B05C 3/02;
(Continued)

(56) References Cited

U.S. PATENT DOCUMENTS 3,381,283 A   4/1968  Gyorgy et al.
3,586,064 A   6/1971  Brown et al.
(Continued)

FOREIGN PATENT DOCUMENTS

DE   3381283       4/1990
EP   0778944 B1   11/1999
(Continued)

OTHER PUBLICATIONS

Corrosionpedia—Diaphragm Pump—Published: Oct. 2, 2014 1 Updated: May 4, 2019 (Year: 2019).
(Continued)

*Primary Examiner* — William P Fletcher, III
(74) *Attorney, Agent, or Firm* — Jeffrey Schox; Annie Imbrie-Moore

(57) ABSTRACT

A system for buoyant particle processing includes: a reaction vessel, a stirring mechanism, a set of one or more pumps, and a filter. The system can additionally or alternatively include a set of pathways and/or any other suitable component(s). A method for buoyant particle processing includes: stirring the contents of a reaction vessel; washing a set of buoyant particles; and filtering the contents of the reaction vessel. Additionally or alternatively, the method can include any or all of: preprocessing the set of buoyant particles; adding a set of inputs to the reaction vessel; washing the set of buoyant particles; repeating one or more; and/or any other suitable process(es).

19 Claims, 8 Drawing Sheets

Related U.S. Application Data continuation of application No. 16/506,865, filed on Jul. 9, 2019, now abandoned.

(60) Provisional application No. 62/695,517, filed on Jul. 9, 2018.

(51) Int. Cl.
| | |
|---|---|
| *B05C 11/10* | (2006.01) |
| *B05C 19/02* | (2006.01) |
| *B05D 1/18* | (2006.01) |
| *B05D 1/22* | (2006.01) |
| *B05D 1/36* | (2006.01) |
| *B05D 5/04* | (2006.01) |
| *C12M 1/00* | (2006.01) |
| *C12M 1/26* | (2006.01) |

(52) U.S. Cl.
CPC ............... *B05D 1/18* (2013.01); *B05D 1/22* (2013.01); *B05D 1/36* (2013.01); *B05D 5/04* (2013.01); *C12M 33/00* (2013.01); *C12M 47/04* (2013.01)

(58) Field of Classification Search
CPC ........ B05C 11/10; B05C 19/02; C12M 33/00; C12M 47/04; C12M 33/14; C12M 47/02; C12M 25/16; B01J 8/006; B01D 24/02
See application file for complete search history.

(56) References Cited

U.S. PATENT DOCUMENTS

| | | | |
|---|---|---|---|
| 3,692,493 A | 9/1972 | Terasaki | |
| 3,920,549 A | 11/1975 | Gigliello et al. | |
| 4,086,060 A | 4/1978 | Hermann | |
| 4,464,254 A | 8/1984 | Dojki et al. | |
| 4,487,700 A | 12/1984 | Kanter | |
| 4,689,151 A | 8/1987 | Kosikowski et al. | |
| 4,714,680 A | 12/1987 | Civin | |
| 4,845,025 A | 7/1989 | Lary et al. | |
| 5,116,724 A | 5/1992 | Delaage et al. | |
| 5,182,192 A | 1/1993 | Steplewski et al. | |
| 5,246,829 A | 9/1993 | Delaage et al. | |
| 5,266,199 A | 11/1993 | Tsukagoshi et al. | |
| 5,339,830 A | 8/1994 | Blake | |
| 5,354,483 A | 10/1994 | Furse | |
| 5,594,164 A | 1/1997 | Bull | |
| 5,639,382 A | 6/1997 | Brown | |
| 5,730,864 A | 3/1998 | Delsalle et al. | |
| 5,853,600 A | 12/1998 | McNeal et al. | |
| 5,874,266 A | 2/1999 | Palsson | |
| 6,036,940 A | 3/2000 | Ju et al. | |
| 6,151,113 A | 11/2000 | Odonohue et al. | |
| 6,221,315 B1 | 4/2001 | Giesler et al. | |
| 6,261,537 B1 | 7/2001 | Klaveness et al. | |
| 6,264,917 B1 | 7/2001 | Klaveness et al. | |
| 6,331,289 B1 | 12/2001 | Klaveness et al. | |
| 6,416,739 B1 | 7/2002 | Rogerson et al. | |
| 6,506,167 B1 | 1/2003 | Ishimoto et al. | |
| 6,528,039 B2 | 3/2003 | Unger | |
| 6,544,424 B1 | 4/2003 | Shevitz | |
| 6,569,340 B2 | 5/2003 | Kopf | |
| 6,652,136 B2 | 11/2003 | Marziali | |
| 6,723,303 B1 | 4/2004 | Quay | |
| 6,919,031 B2 | 7/2005 | Blumenschein et al. | |
| 7,524,641 B2 | 4/2009 | Jurgensen et al. | |
| 7,704,393 B2 | 4/2010 | Noh et al. | |
| 8,048,320 B2 | 11/2011 | Leach et al. | |
| 8,066,127 B2 | 11/2011 | Coelho et al. | |
| 8,177,072 B2 | 5/2012 | Chapman et al. | |
| 8,513,032 B2 | 8/2013 | Jablonski et al. | |
| 8,540,082 B2 | 9/2013 | Kelland et al. | |
| 8,747,289 B2 | 6/2014 | Coelho | |
| 8,835,186 B2 | 9/2014 | Jablonski et al. | |
| 9,011,819 B2 | 4/2015 | Rychak | |
| 9,039,999 B2 | 5/2015 | Campton et al. | |
| 9,120,095 B2 | 9/2015 | OConnell | |
| 9,234,890 B2 | 1/2016 | Adams et al. | |
| 9,599,545 B2 | 3/2017 | Coelho | |
| 9,695,394 B1 | 7/2017 | Coelho et al. | |
| 9,766,237 B2 | 9/2017 | Jablonski et al. | |
| 9,797,817 B2 | 10/2017 | McNaughton et al. | |
| 9,821,111 B2 | 11/2017 | Coelho et al. | |
| 9,857,361 B2 | 1/2018 | Wanders et al. | |
| 10,195,547 B2 | 2/2019 | McNaughton et al. | |
| 10,302,536 B2 | 5/2019 | Shi et al. | |
| 10,479,976 B2 | 11/2019 | Shi et al. | |
| 10,585,088 B2 | 3/2020 | Gohel et al. | |
| 10,684,172 B2 | 6/2020 | Carron et al. | |
| 10,794,900 B2 | 10/2020 | Wanders et al. | |
| 10,859,477 B2 | 12/2020 | Nakamura et al. | |
| 10,934,519 B2 | 3/2021 | Roy et al. | |
| 11,007,285 B2 | 5/2021 | Butts et al. | |
| 11,291,931 B2 | 4/2022 | McNaughton et al. | |
| 11,583,893 B2* | 2/2023 | McNaughton ......... C12M 33/14 | |
| 11,819,842 B2 | 11/2023 | Wegner et al. | |
| 2003/0104359 A1 | 6/2003 | Cuthbertson et al. | |
| 2004/0023222 A1 | 2/2004 | Russell et al. | |
| 2004/0166029 A1 | 8/2004 | Losada et al. | |
| 2005/0059163 A1 | 3/2005 | Dastane et al. | |
| 2006/0054191 A1 | 3/2006 | Higuchi et al. | |
| 2006/0131236 A1 | 6/2006 | Belfort et al. | |
| 2007/0015191 A1 | 1/2007 | Bitner et al. | |
| 2007/0036722 A1 | 2/2007 | Rongved et al. | |
| 2007/0075016 A1 | 4/2007 | Leach | |
| 2007/0190584 A1 | 8/2007 | Jurgensen et al. | |
| 2008/0034509 A1 | 2/2008 | Nuennerich et al. | |
| 2009/0042284 A1 | 2/2009 | Tachibana et al. | |
| 2010/0285606 A1 | 11/2010 | Phillips et al. | |
| 2011/0236884 A1 | 9/2011 | Jablonski et al. | |
| 2012/0202225 A1 | 8/2012 | Knutson et al. | |
| 2013/0029411 A1 | 1/2013 | Roy et al. | |
| 2013/0280767 A1* | 10/2013 | Kobayashi ............. B01D 71/68 |
| | | | 435/115 |
| 2014/0161688 A1 | 6/2014 | Campton et al. | |
| 2014/0277672 A1 | 9/2014 | Manzarek et al. | |
| 2015/0011013 A1 | 1/2015 | Campton et al. | |
| 2015/0021963 A1 | 1/2015 | Reed | |
| 2015/0219636 A1 | 8/2015 | Rychak et al. | |
| 2015/0260178 A1 | 9/2015 | Giessbach | |
| 2015/0320924 A1 | 11/2015 | Flieg et al. | |
| 2017/0183619 A1 | 6/2017 | Coelho et al. | |
| 2018/0171295 A1 | 6/2018 | Shi et al. | |
| 2020/0009614 A1 | 1/2020 | McNaughton et al. | |
| 2020/0072834 A1 | 3/2020 | Busa et al. | |
| 2020/0276540 A1 | 9/2020 | Smyslova et al. | |
| 2021/0180108 A1 | 6/2021 | Kim et al. | |
| 2023/0314428 A1 | 10/2023 | Snow et al. | |

FOREIGN PATENT DOCUMENTS

| | | |
|---|---|---|
| EP | 1073716 B1 | 4/2004 |
| EP | 2104488 B1 | 10/2016 |
| GB | 1407267 A | 9/1975 |
| JP | 2001120964 A | 5/2001 |
| JP | 2014521333 A | 8/2014 |
| WO | 2012090863 A1 | 7/2012 |
| WO | 2013096157 A1 | 6/2013 |
| WO | 2015133972 A1 | 9/2015 |
| WO | 2017109072 A1 | 6/2017 |
| WO | 2017190117 A1 | 11/2017 |

OTHER PUBLICATIONS https://en.wikipedia.org/wiki/Diaphragm_pump (Year: 2021).
https://www.yamadapump.com/what-is-a-double-diaphragm-pump/#:-:text=A (Year: 2021).
Mud Sucker Diaphragm Pumps, https://wastecorp.com/ms-faqs (Year: 2021)
Wang, Meiyao , "Quantifying CD4 receptor protein in two human CD4+ lymphocyte preparations for quantitative flow cytometry",

(56) References Cited

OTHER PUBLICATIONS

Clinical proteomics, 11 (1 ), 43. https:// doi.org/10.1186/1559-0275-11-43.

* cited by examiner

SYSTEM AND METHOD FOR BUOYANT PARTICLE PROCESSING

CROSS-REFERENCE TO RELATED APPLICATIONS

This application is a continuation of U.S. application Ser. No. 17/679,688, filed 24 Feb. 2022, which is a continuation of U.S. application Ser. No. 16/506,865, filed 9 Jul. 2019, which claims the benefit of U.S. Provisional Application Ser. No. 62/695,517, filed 9 Jul. 2018, each of which is incorporated herein in its entirety by this reference. This application is related to U.S. Application Ser. No. 16/004,874, filed 11 Jun. 2018, which is a continuation-in-part of U.S. application Ser. No. 14/969,446, filed 15 Dec. 2015, which claims the benefit of U.S. Provisional Application Ser. No. 62/092,019, filed on 15 Dec. 2014 and U.S. Provisional Application Ser. No. 62/189,518 filed on 7 Jul. 2015, which are each incorporated herein in their entirety by this reference.

TECHNICAL FIELD

This invention relates generally to separation methods and systems in the field of biological and chemical sample processing. More specifically, it relates to an improved system and method for the manufacture of buoyant particles used in the field of biological and chemical sample processing.

BACKGROUND

In research and diagnostic applications, it is often important to be able to isolate one or more types of particles of a sample. Isolation of target components in an efficient and high throughput manner can thus have a significant impact in healthcare applications, biological research, research in the food industry, bioprocessing, fermentation, and medical research. Components for isolation and extraction can include cells, proteins, nucleic acids, lipids, chemical compounds, and other particles commonly found in biological fluid. Buoyant particles have been shown to be useful in these applications. Manufacturing and preparing buoyant particles suitable for these applications, however, can be a very challenging process, as well as require large amounts of user intervention to perform.

Thus, there is a need in the biological and chemical sample processing field to create an improved method and system for buoyant particle processing. This invention provides such an improved method and system.

DESCRIPTION OF THE PREFERRED EMBODIMENTS

The following description of preferred embodiments and examples of the invention is not intended to limit the invention to these preferred embodiments and examples, but rather to enable any person skilled in the art to make and use this invention.

1. Overview

Figure 1:
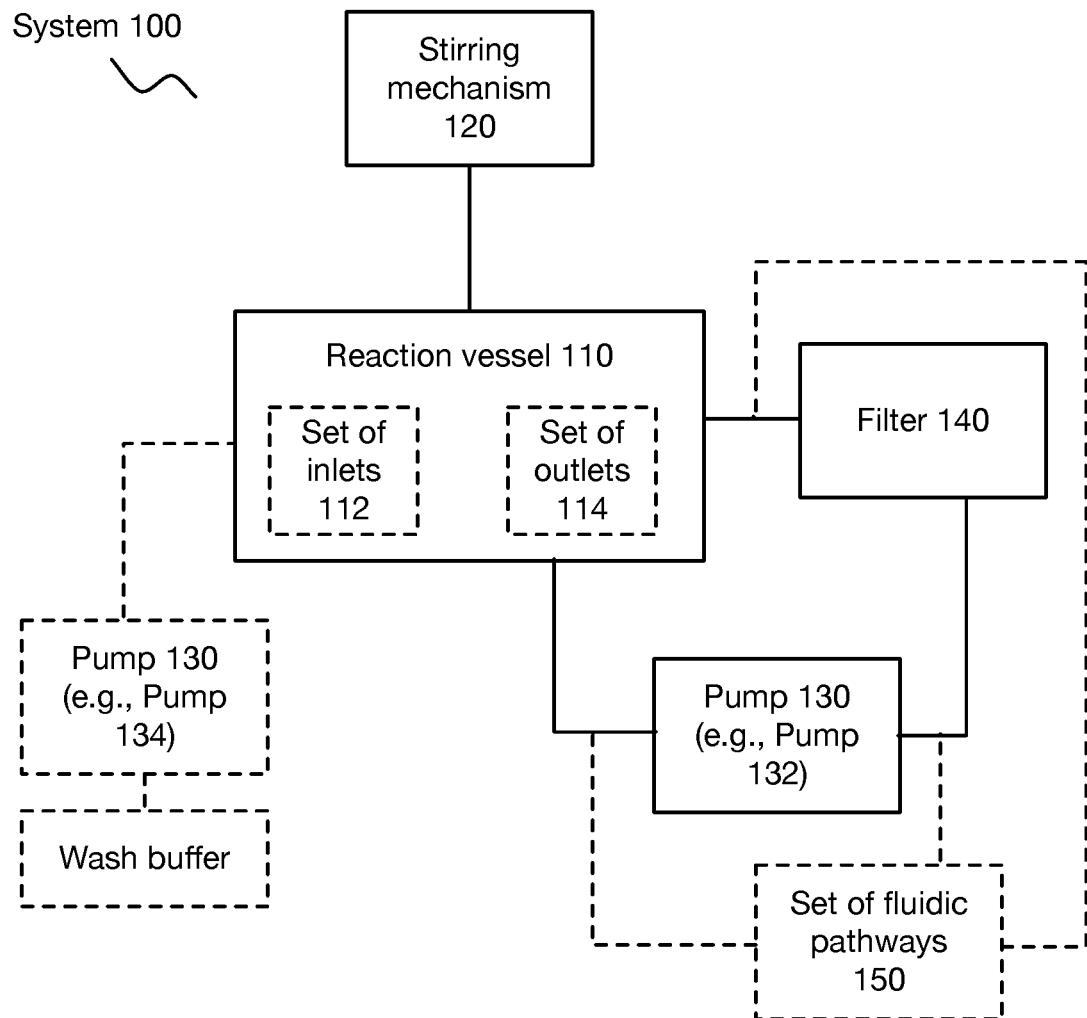
FIG. 1 depicts a variation of the system 100 for buoyant particle processing.

As shown in FIG. 1, a system 100 for buoyant particle processing includes: a reaction vessel 110, a stirring mechanism 120, a set of one or more pumps 130, and a filter 140. The system 100 can additionally or alternatively include a set of pathways 150 and/or any other suitable component(s).

Figure 2:
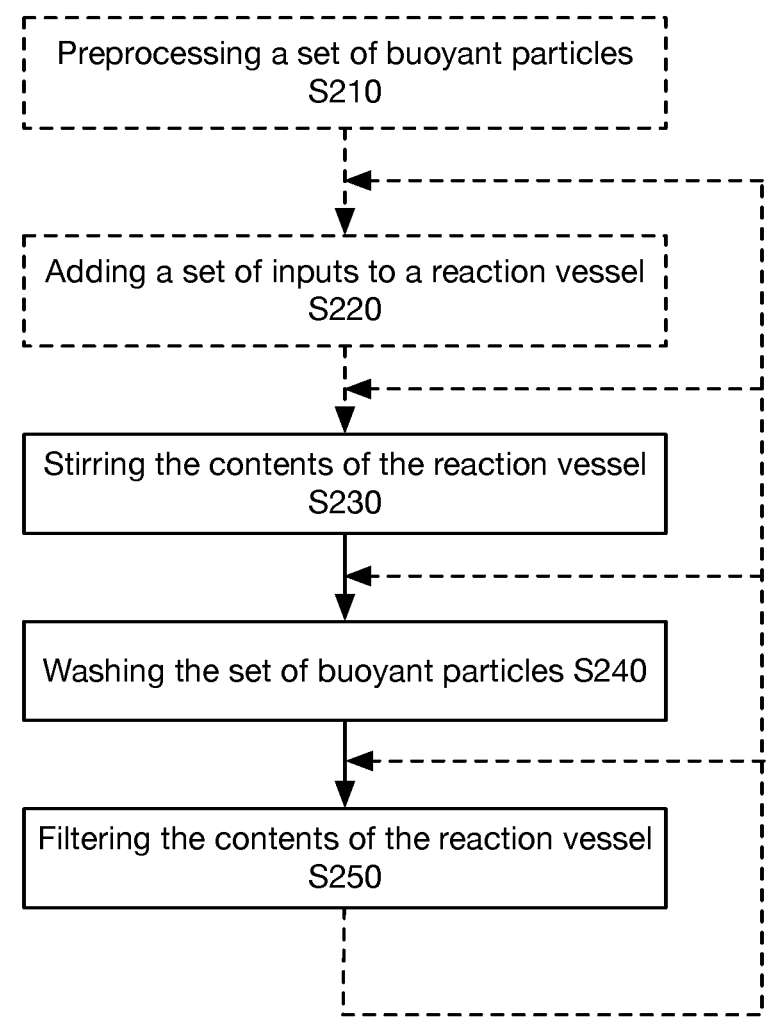
FIG. 2 depicts a variation of the method 200 for buoyant particle processing.

As shown in FIG. 2, a method 200 for buoyant particle processing includes: stirring the contents of a reaction vessel S230; washing a set of buoyant particles S240; and filtering the contents of the reaction vessel S250. Additionally or alternatively, the method 200 can include any or all of: preprocessing the set of buoyant particles S210; adding a set of inputs to the reaction vessel S220; repeating one or more processes (e.g., S230 through S250); and/or any other suitable process(es).

2. Benefits

The system and/or method can confer several benefits over conventional systems and methods buoyant particle processing.

First, in some variants, the system and/or method can confer the benefit of producing and/or modifying buoyant particles, thereby configuring them for separating and/or isolating any or all of: cells, bacteria, viruses, exosomes and vesicles, molecules, DNA, RNA, or any other suitable particle(s) from a suspension or solution. In a set of specific examples, for instance, a set of buoyant particles are produced which serve as an affinity support for molecular separation.

Second, in some variants, the system and/or method can confer the benefit of producing and/or modifying buoyant particles, thereby configuring them for any or all of: animal, plant, and microbial culture. In a set of specific examples, for instance, a set of buoyant particles are processed such that a surface of the buoyant particle acts as a buoyant platform during any or all of the cell culture and proliferation process.

Third, in some variants, the system and/or method can confer the benefit of producing and/or modifying buoyant particles, thereby configuring them to provide a chemical and/or physical stimulus to a cell through direct contact and/or through elution of the stimulus into a solution.

Fourth, in some variants, the system and/or method can confer the benefit of producing and/or modifying buoyant particles, thereby configuring them to serve as and/or display a chemical catalyst for use in the catalysis of chemical reactions.

Fifth, in some variants, the system and/or method can confer the benefit of minimizing and/or preventing buoyant particle breakage within an automated and/or semi-automated buoyant particle processing system (e.g., manufacturing system). In a set of specific examples, for instance, a system for processing buoyant particles includes a diaphragm pump (e.g., quaternary 4-piston diaphragm pump) to circulate a set of buoyant particles throughout the system, which can minimize a number of buoyant particles which are crushed while passing through the pump (e.g., in comparison with a peristaltic pump).

Sixth, in some variants, the system and/or method can confer the benefit of enabling an efficient and scalable filtering of buoyant particles (e.g., from debris, from a wash solution, from a buffer, from a subset of relatively small buoyant particles, from a subset of relatively large buoyant particles, etc.). In a set of specific examples, for instance, a system for processing buoyant particles includes a hollow fiber module configured for tangential flow filtering, which functions to separate buoyant particles from a remainder of a solution with minimal clogging of the system due to buoyant particle flotation and the flow of the remaining solution.

Seventh, in some variants, the system and/or method can confer the benefit of enabling any or all of: a semi-automated, fully automated, scalable, and large-scale system and method for buoyant particle processing. In a set of specific examples, for instance, the system and/or method confer the benefit of constantly and consistently circulating (e.g., through a set of pumps, a tangential flow filter, and a prescribed set of flow parameters) a set of buoyant particles during a set of processes, wherein the circulation prevents clogging while performing the prescribed set of processes (e.g., washes, chemical additions, particle etching, filtering, etc.).

Eighth, in some variants, the system and/or method can confer the benefit of minimizing user input and/or user performance in any or all of buoyant particle processing. In a set of specific examples, a set of centrifuging steps used in conventional mixing processes are replaced with automated buoyant particle circulation and stirring. In another set of specific examples, the system can be partially or fully closed, which can eliminate or at least minimize required user intervention. In an alternative variant, the system can interface with a centrifuge and/or the method can include one or more centrifugation processes. In a specific example, for instance, one or more materials (e.g., linkers) are processed with a centrifuge prior to entering the system 100.

Additionally or alternatively, the system and/or method can confer any suitable benefit over conventional systems and methods for buoyant particle processing.

3. System 100

The system 100 functions to produce a processed set of buoyant particles. Additionally or alternatively, the system 100 can function to minimize and/or eliminate breakage of a set of buoyant particles during buoyant particle processing; minimize and/or eliminate user intervention during buoyant particle processing (e.g., in comparison with conventional buoyant particle processing systems); enable a scaling up of a buoyant particle processing (e.g., prevent clogging of buoyant particles); enable the production of a uniform (e.g., in surface modification, in size, etc.) set of buoyant particles; and/or perform any other suitable function.

The system 100 receives as an input a set of buoyant particles. Additionally or alternatively, the system 100 can receive other inputs, such as a set of processing materials, which can include—but is not limited to including—any or all of: chemicals (e.g., functional groups, linkers, etc.), proteins, buffers, reagents, washes, and/or any other suitable materials for maintaining, modifying, or otherwise interacting with the set of buoyant particles.

Each of the set of buoyant particles (equivalently referred to herein as substrates) is preferably a microbubble (e.g., having a micron-scale diameter, having a diameter less than 1000 microns, having a diameter less than 100 microns, having a diameter between 10 and 100 microns, having a diameter of 50 microns, etc.), but can additionally include a nanobubble (e.g., having a nanometer-scale diameter, having a diameter less than 1 micron, etc.), and/or any other suitable set of buoyant particles. The set of buoyant particles received as an input to the system 100 are further preferably raw (e.g., unprocessed, absent of surface modifications, only washed, etc.) or partially processed (e.g., glass coated in silane, glass coated in plastic, having a first surface modification, having a subset of surface modifications, polished, etched, etc.), but can additionally or alternatively be processed in any other suitable way to any suitable degree. In examples, the buoyant particles have a diameter between 10 nm and 100 nm (e.g., for use in targeting analytes in a subsequent protocol). In other examples, the buoyant particles have a diameter between 1 μm and 30 μm (e.g., for use in targeting cells in a subsequent protocol); however, the particles can have any other suitable dimension (e.g., diameter configured to enable the buoyant particles to be included in the retentate of a tangential flow filter as described below).

The set of buoyant particles (e.g., beads, spheres, micelles, microbubbles) can include any one or more of: plastic beads (e.g., polypropylene beads, polyethylene beads, etc.), glass beads, lipid beads (e.g., stabilized liposome-based beads), hollow beads, solid beads, liquid-filled beads, gas-filled beads, and any other suitable type of particle.

The set of buoyant particles are preferably characterized by a first density lower than that of the density (i.e., a second density) of surrounding fluids (e.g., buffers, solvents, fluids ranging from 0.1 g/cm$^3$ and 0.99 g/cm$^3$, etc.). As such, the buoyant particles are preferably configured to float when placed within the surrounding fluids and/or fluids in a subsequent separation protocol, such as a separation protocol described in U.S. Application Ser. No. 16/004,874, filed 11 Jun. 2018, which is incorporated herein in its entirety by this reference. However, buoyant particles can alternatively be configured with any other suitable density relative to that of the other inputs to the system.

In one variation, the set of buoyant particles includes microbubbles (e.g., gas-filled microparticles, hollow microspheres, colloidal bubbles) that can be spheroidal, skirted, ellipsoidal or any other suitable three-dimensional shape. The shape of the microbubbles can vary dynamically in response to the fluid dynamics of surrounding solutions (e.g., changing from one shape to another dictated by gravity, viscosity, and surface tension), but can alternatively be a fixed shape. In a specific example, the microbubbles are composed of borosilicate glass that can include a particle shell surrounding a particle core (e.g., gas filled, fluid-filled, particle-filled, etc.). However, the particle shell can be alternatively composed of any other suitable material including lipids, proteins, surfactants, polymers, and/or any suitable combination thereof. In this example, the glass microbubbles can be fabricated with a fixed spheroidal shape defining a particle diameter (e.g., ranging from between 5 to 30 micron), and a particle shell thickness (e.g., less than 2 micron thick). However, the buoyant particles can be of any other suitable composition, shape, density, and/or dimension.

The system 100 produces as an output a set of processed buoyant particles, wherein the processed buoyant particles refer to the input buoyant particles having undergone one or more surface modifications (e.g., through method 200 described below). The surface modifications preferably include the application of one or more layers (e.g., chemistries) applied to the buoyant particle surface, wherein the layers include any or all of: molecules, chemicals, moieties, proteins, organic materials, inorganic materials, protective shells, or any other suitable materials. In some variations, for instance, the layers are formed by the solution-based sequential addition of molecules onto the bubble. Additionally or alternatively, surface modifications can be applied by any or all of: in situ polymerization, chemical vapor deposition, polymeric coating in the presence of a solvent, polymeric coating in the absence of a solvent, etching, or otherwise modifying the surface of the input set of buoyant particles.

Each of the surface modifications (e.g., layers) preferably functions to facilitate binding, such as any or all of: binding with the buoyant particle surface (e.g., for a $1^{st}$ layer as described below), binding with a previously applied (e.g., lower) surface modification (e.g., for a $2^{nd}$ layer to bind with a $1^{st}$ layer, for a $3^{rd}$ layer to bind with a $2^{nd}$ layer, etc.), binding with a subsequently applied (e.g., above) surface modification (e.g., for a $1^{st}$ layer to bind with a $2^{nd}$ layer, for a $2^{nd}$ layer to bind with a $3^{rd}$ layer, etc.), binding with a target material (e.g., solution, compound, material, cell, etc.) in subsequent applications (e.g., cell separation), or any other suitable binding. Additionally or alternatively, any or all of the surface modifications can function to prevent binding (e.g., $2^{nd}$ layer having a long chemical chain configured to prevent binding between the $1^{st}$ and $3^{rd}$ layers, $2^{nd}$ layer having a long chemical chain configured to prevent binding between the $3^{rd}$ layer and the buoyant particle surface, etc.), enhance buoyant particle longevity (e.g., shell to prevent breakage), prevent buoyant particle leeching (e.g., shell to prevent leeching on buoyant particle inner contents), and/or perform any other suitable function.

In some variations, the processed buoyant particles include buoyant particles functionalized with moieties for binding to a target constituent (e.g., red blood cells, white blood cells, T-cells, circulating tumor cells, stem cells, circulating nucleic acids, etc.) and can include any one or more of: charge-based moieties, nucleic acid-targeting moieties, protein-based moieties (e.g., cell adhesion molecules, growth factors, synthetic proteins), and any other suitable moiety. In a specific example, a particle shell of glass microbubbles can be coated with an aminosilane layer to allow for subsequent surface functionalization with biomolecules (e.g., antibodies, aptamers, lectins, oligos, molecular barcodes, etc.). After glass microbubbles have been aminofunctionalized, the glass microbubbles are preferably crosslinked to streptavidin. However, any other suitable chemical procedure can be performed for surface functionalization of the substrates (e.g., PEGylation, click chemistry, layer-by-layer assembly, ink-jet printing etc.) for selective capture of target constituents, using any other suitable moiety. The buoyant particles can additionally and/or alternatively function as a signal delivery agent to target constituents (e.g., via a recombinant molecule bound to the surface of the substrate particle). In a specific example, CD3+ T cells can be captured using a microbubble displaying Cd28, a protein which can stimulate the T cell (e.g., inducing cell proliferation and cytokine production), a primary step to manufacturing T cells expressing a chimeric antigen receptor (e.g., CAR-T cells) used in cell therapy (e.g., cancer treatment). However, the substrates can be otherwise configured with any other suitable moiety for multifunctional applications including target-bound complex separation and extraction.

Each of the set of processed buoyant particles preferably includes a $1^{st}$ layer (e.g., including one or more moieties as described above), equivalently referred to herein as the base layer, which functions to bind with the buoyant particle surface. Additionally or alternatively, the $1^{st}$ layer can function to prevent nonspecific binding by preventing binding between subsequent layers and the buoyant particle surface (e.g., by uniformly coating the buoyant particle surface). The $1^{st}$ layer interfaces with (e.g., is applied to, layered on, functionalized with, etc.) the input buoyant particle surface (e.g., raw surface, silane surface, etc.). Additionally or alternatively, the $1^{st}$ layer can interface with a subsequent layer (e.g., $2^{nd}$ layer as described below, $3^{rd}$ layer as described below, $4^{th}$ layer, $5^{th}$ layer, etc.), a target material for capture in a separation process, and/or any other suitable material(s).

The $1^{st}$ layer is preferably covalently bound to the buoyant particle surface and configured for uniform particle coating (e.g., preventing patchiness in each particle coating, uniformly coating all of the input set of buoyant particles, etc.). The $1^{st}$ layer is further preferably applied as a uniform monolayer coating as opposed to nonuniform polymeric coating (e.g., a carpet layer coating).

For glass (e.g., glass with a silane surface) buoyant particles, the $1^{st}$ layer preferably includes one or more amino groups. In a specific example, an aminosilane group of the $1^{st}$ layer interacts with a hydroxyl group on the surface of a glass buoyant particle. Additionally or alternatively, the $1^{st}$ layer can include any suitable groups or other components.

The $1^{st}$ layer is preferably composed of multiple subcomponents (e.g., chemical compounds, proteins, molecules, etc.) linked together, which can each have a different function and/or target (e.g., $1^{st}$ subcomponent is configured to bind with the buoyant particle surface and $2^{nd}$ subcomponent is configured to bind with a subcomponent of a $2^{nd}$ layer). Alternatively, the $1^{st}$ layer can include a single subcomponent, the multiple subcomponents can have the same function and/or target, and/or the $1^{st}$ layer can have any other suitable structure.

In some variations, the $1^{st}$ layer includes a first subcomponent, herein referred to as the "A element," connected (e.g., linked, bonded, etc.) to a second subcomponent, herein referred to as the "B element," wherein the A element is configured to bind (e.g., covalently, in a reaction occurring in boiling toluene, etc.) with a surface of the buoyant particle, and wherein the B element is configured to bind with any or all of: a subsequent layer (e.g., $2^{nd}$ layer, $3^{rd}$ layer, etc.), a target element (e.g., target molecule, target cell, etc.), or any other suitable component.

Figure 4:
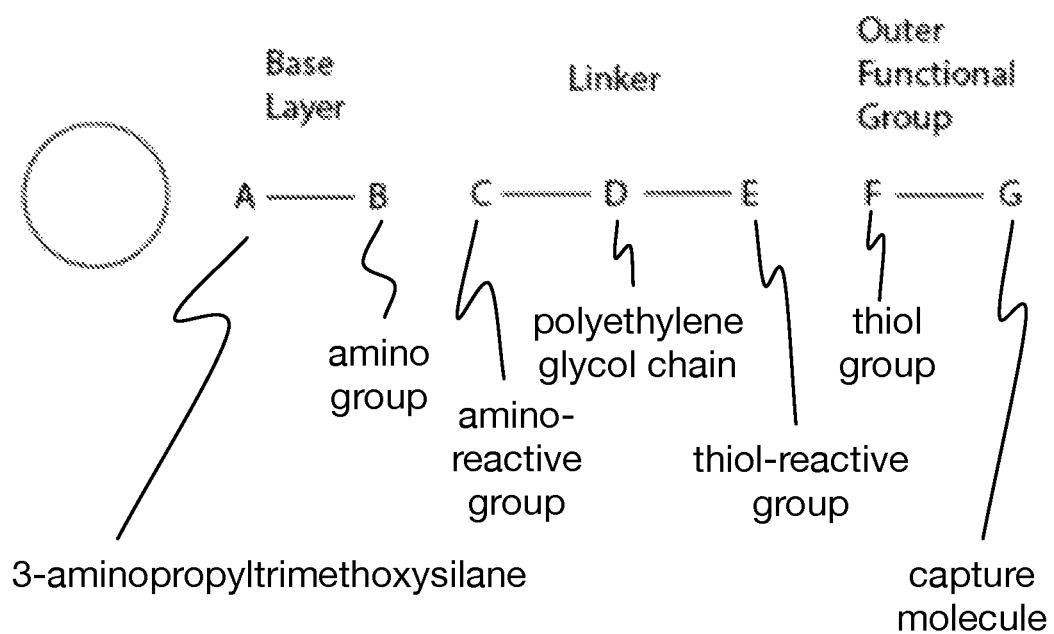
FIG. 4 depicts a specific example of a variation of a processed buoyant particle.
Figure 5A:
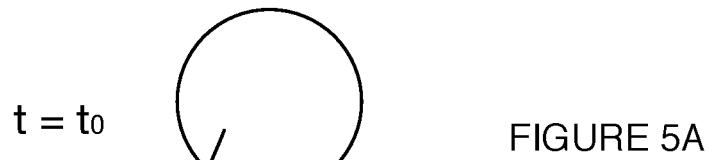
FIGS. 5A-5D depict a variation of a buoyant particle at various stages of the method 200.
Figure 5B:
Figure 5C:
Figure 5D:
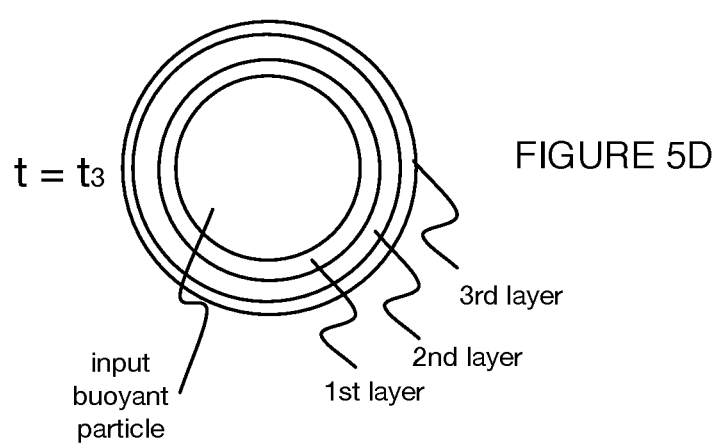

In a first specific example (e.g., as shown in FIG. 4), the A element includes the trimethoxysilane portion of 3-aminopropyltrimethoxysilane, which is configured to covalently bind with the buoyant particle surface (e.g., silane coated glass), and the B element includes the 3-aminopropyl portion of 3-aminopropyltrimethoxysilane, which is configured to bind with a $2^{nd}$ layer (e.g., as described below).

Each of the set of processed buoyant particles can optionally include a $2^{nd}$ layer (e.g., in combination with the $1^{st}$ layer, in absence of a $1^{st}$ layer, etc.), equivalently referred to herein as the linker layer, which is preferably configured to bind with the $1^{st}$ layer (e.g., a B element of the $1^{st}$ layer). The linker layer can additionally or alternatively be configured to bind with a subsequent layer (e.g., an F element of a $3^{rd}$ layer), a target element, or any other suitable material. The $2^{nd}$ layer preferably functions to increase a distance between a $1^{st}$ layer (and/or the buoyant particle surface) and a subsequent layer (and/or a target element), such as a $3^{rd}$ layer (e.g., as described below). This can additionally or alternatively function to prevent binding between a subsequent layer with a $1^{st}$ layer (and/or the buoyant particle surface), prevent binding between a target element and a previous layer (and/or the buoyant particle surface), facilitate capture of a target element (e.g., for a $2^{nd}$ layer having a capture molecule), and/or perform any other suitable function. Further additionally or alternatively, the $2^{nd}$ layer (e.g., a D element of the $2^{nd}$ layer as described below) can be configured to be cleavable (e.g., to permit analyte release and/or cell release following capture). As such, one or more subcomponents (e.g., $2^{nd}$ subcomponent, $1^{st}$ subcomponent, $3^{rd}$ subcomponent, etc.) can include any or all of: disulfide bonds susceptible to chemical reduction, polysaccharide chains susceptible to glycosidase digestion, polypeptide chains susceptible to peptidase digestion, DNA chains susceptible to endonucleases (e.g., restriction-type endonucleases), and/or any other suitable materials and/or features. Additionally or alternatively, any other suitable layer can be configured to be cleavable.

The $2^{nd}$ layer preferably interfaces with (e.g., is applied to, layered on, functionalized with, bound to, etc.) the $1^{st}$ layer (e.g., a B element of the $1^{st}$ layer, an A element of the $1^{st}$ layer, etc.). Additionally or alternatively, the $2^{nd}$ layer can interface with any or all of: a subsequent layer (e.g., a $3^{rd}$ layer, a $4^{th}$ layer, etc.), a target element, the buoyant particle surface, or any other suitable material.

In preferred variations, there is minimal or no binding between the $2^{nd}$ layer and the buoyant particle surface (e.g., enabled by a uniform coating of the buoyant particle surface by the $1^{st}$ layer, enabled by a choice of a B element of the $2^{nd}$ layer, etc.). Alternatively, binding can occur (e.g., accidentally, in regions having a sparse distribution of a $1^{st}$ layer, etc.).

The $2^{nd}$ layer is preferably composed of multiple subcomponents (e.g., chemical compounds, proteins, molecules, etc.) linked (e.g., bound) together, which can each have a different function and/or target (e.g., one subcomponent is configured to bind with a subcomponent of the $1^{st}$ layer and another subcomponent is configured to bind with a subcomponent of a subsequent layer). Alternatively, the $2^{nd}$ layer can include a single subcomponent, the multiple subcomponents can have the same function and/or target, and/or the $2^{nd}$ layer can have any other suitable structure.

In some variations, the $2^{nd}$ layer includes a first subcomponent, herein referred to as the "C element," connected (e.g., linked, bonded, etc.) to a second subcomponent, herein referred to as the "D element," which is connected to a third subcomponent, herein referred to as the "E element." The C element is preferably configured to bind (e.g., covalently) with a B element of the $1^{st}$ layer and the D element; and the E element is configured to bind with the D element and a subsequent layer (e.g., $3^{rd}$ layer, $4^{th}$ layer, etc.). Additionally or alternatively, the $2^{nd}$ layer can be configured to bind with a target element (e.g., target molecule, target cell, etc.), and/or any other suitable component.

In additional or alternative variations, the $2^{nd}$ layer can include two subcomponents (e.g., a C element connected to an E element), a single subcomponent, additional subcomponents, and/or any suitable number of subcomponents arranged in any suitable way.

In a first specific example of the $2^{nd}$ layer, the C element includes an amino-reactive group (e.g., N-hydroxysuccinimide [NHS] ester) configured to bind (e.g., under predetermined conditions) to an amino group (e.g., B element) of the $1^{st}$ layer; the D element (e.g., polyethylene glycol, polyethylene glycol chain, etc.) includes an interposed region of a predetermined length (e.g., 12 repeat units, 24 repeat units, less than 12 repeat units, greater than 12 repeat units, less than 30 repeat units, etc.), the D element configured to bind to the C element and the E element; and the E element includes a thiol-reactive group (e.g., maleimide) configured to bind with a subsequent layer (e.g., F element of a $3^{rd}$ layer as described below) and/or a target material.

Each of the set of processed buoyant particles can optionally include a $3^{rd}$ layer (e.g., in combination with the $1^{st}$ and $2^{nd}$ layers, in absence of one or both of the $1^{st}$ and $2^{nd}$ layers, etc.), equivalently referred to herein as the outer functional group, which is preferably configured to bind with the $2^{nd}$ layer (e.g., an E element of the $2^{nd}$ layer). The linker layer can additionally or alternatively be configured to bind with a subsequent layer (e.g., a $4^{th}$ layer), the $1^{st}$ layer, the buoyant particle surface, a target element, or any other suitable material. The $3^{rd}$ layer preferably functions to bind with (e.g., and therefore capture) a target material. Additionally or alternatively, the $3^{rd}$ layer can function to prevent binding between the target material and a previous layer and/or perform any other suitable function.

The $3^{rd}$ layer preferably interfaces with (e.g., is applied to, layered on, functionalized with, bound to, etc.) the $2^{nd}$ layer (e.g., an E element of the $2^{nd}$ layer, a D element of the $2^{nd}$ layer, a C element of the $2^{nd}$ layer, etc.). Additionally or alternatively, the $3^{rd}$ layer can interface with any or all of: a subsequent layer (e.g., a layer, a $4^{th}$ layer, a $5^{th}$ layer, etc.), an intermediate layer arranged after the $2^{nd}$ layer, a target element, the buoyant particle surface, or any other suitable material.

In preferred variations, there is minimal or no binding between the $3^{rd}$ layer and the buoyant particle surface (e.g., enabled by a uniform coating of the buoyant particle surface by the $1^{st}$ layer, enabled by a choice of an F element of the $3^{rd}$ layer, etc.) as well as minimal or no binding between the $3^{rd}$ layer and the $1^{st}$ layer. Alternatively, binding can occur (e.g., accidentally, in regions having a sparse distribution of a $1^{st}$ layer, etc.).

The $3^{rd}$ layer is preferably composed of multiple subcomponents (e.g., chemical compounds, proteins, molecules, etc.) linked (e.g., bound) together, which can each have a different function and/or target (e.g., one subcomponent is configured to bind with a subcomponent of the $2^{nd}$ layer another subcomponent is configured to bind with a target material). Alternatively, the $3^{rd}$ layer can include a single subcomponent, the multiple subcomponents can have the same function and/or target, and/or the $3^{rd}$ layer can have any other suitable structure.

In some variations, the $3^{rd}$ layer includes a first subcomponent, herein referred to as the "F element," connected (e.g., linked, bonded, etc.) to a second subcomponent, herein referred to as the "G element." The F element is preferably configured to bind (e.g., covalently) with an E element of the $2^{nd}$ layer and the G element is configured to bind with a target element (e.g., target molecule, target cell, etc.). Additionally or alternatively, the $3^{rd}$ layer can be configured to bind with a subsequent (e.g., $4^{th}$ layer $5^{th}$ layer, etc.), the $1^{st}$ layer, a surface of the buoyant particle, and/or any other suitable component.

In additional or alternative variations, the $3^{rd}$ layer can include a single subcomponent, more than two subcomponents, and/or any suitable number of subcomponents arranged in any suitable way.

In a first specific example of the $3^{rd}$ layer, the F element includes a thiol group configured to bind to a thiol-reactive group (e.g., E element) of the $2^{nd}$ layer, and the G element includes a capture element (e.g., capture molecule, capture group, streptavidin, one or more antibodies, a lectin, an oligonucleotide sequence, etc.) configured to bind with a target material (e.g., a biotinylated species).

The processed buoyant particle can additionally or alternatively include any number of surface modifications arranged (e.g., layered) in any suitable way. In some variations, additional or alternative to those described above, the processed buoyant particle includes any or all of: one or more proteins (e.g., polymerized glycidol) which can function, for instance to increase a surface roughness of the buoyant particle (e.g., and therefore improve a binding ability of the buoyant particle); a shell (e.g., polymer shell) which can function, for instance, to prevent leeching of one or more components of the buoyant particle (e.g., glass buoyant particle) into the surrounding solution; and a change in charge (e.g., applied charge, induced charge, switched charge, etc.) of the buoyant particle surface which can function, for instance, to enable DNA capture (e.g., based on charge switching of silica).

Figure 3:
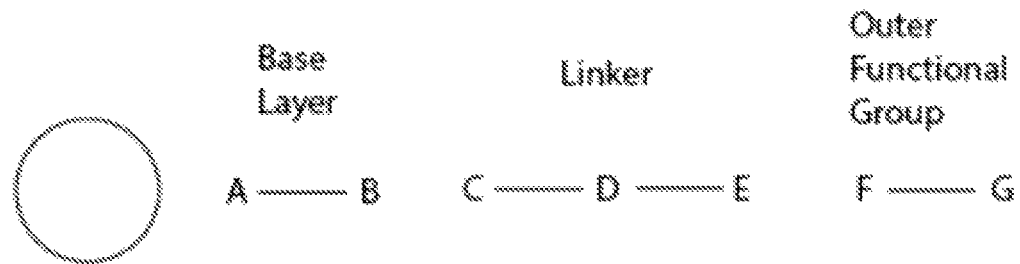
FIG. 3 depicts a variation of a processed buoyant particle.

In a first variation (e.g., as shown in FIG. 3, as shown in FIGS. 5A-5D, etc.), the processed buoyant particle includes a $1^{st}$ layer bound to the buoyant particle surface, a $2^{nd}$ layer bound to the $1^{st}$ layer (e.g., to a B element of the $1^{st}$ layer), and a $3^{rd}$ layer bound to the $2^{nd}$ layer (e.g., to an E element of the $2^{nd}$ layer). In a specific example, the processed buoyant particle includes a $1^{st}$ layer of 3-aminopropyltrimethoxysilane bound to an amino group; a $2^{nd}$ layer of an amino-reactive group configured to bind with the amino group of the $1^{st}$ layer, a polyethylene glycol chain bound to the amino-reactive group, and a thiol-reactive group bound to the polyethylene glycol chain; and a $3^{rd}$ layer of a thiol group configured to bind with the thiol-reactive group of the $2^{nd}$ layer, and a capture molecule.

Figure 6A:
FIGS. 6A-6C depict a variation of a buoyant particle at various stages of the method 200.
Figure 6B:
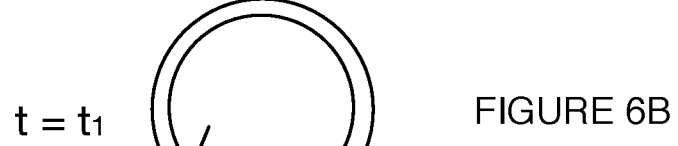
Figure 6C:
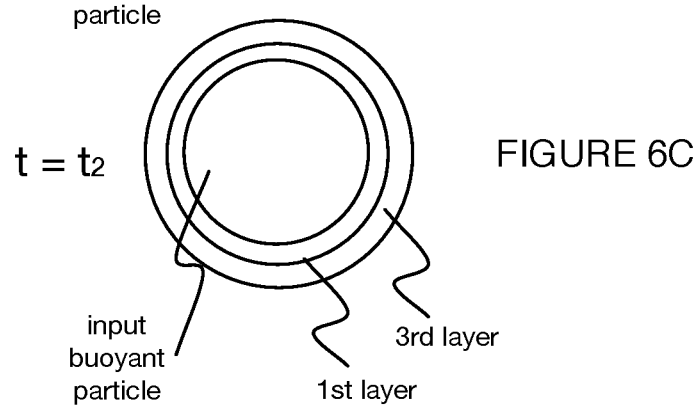

In a second variation (e.g., as shown in FIGS. 6A-6C), the processed buoyant particle includes a $1^{st}$ layer bound to the buoyant particle surface and a $3^{rd}$ layer bound to the $1^{st}$ layer.

In a third variation, the processed buoyant particle includes a buoyant particle having a surface with an altered charge density.

3.1 System: Reaction Vessel 110

The system 100 includes a reaction vessel 110, equivalently referred to herein as a process chamber, which functions to contain the set of buoyant particles and any suitable solutions (e.g., buffers, solvents, etc.) during one or more processing steps (e.g., while coated in one or more layers, while etched, etc.). Additionally or alternatively, the reaction vessel 110 can function to enable an even coating of each of the set of buoyant particles, such as by having a size above a predetermined threshold such that the buoyant particles can have a particle-to-particle spacing above a predetermined threshold, maintain a proper environment (e.g., temperature, humidity, etc.) for buoyant particle processing (e.g., heating the set of particles, boiling a solution, cooling the set of particles, etc.), and/or perform any other suitable function.

The reaction vessel 110 receives the set of buoyant particles (e.g., input set of buoyant particles, partially processed buoyant particles, processed buoyant particles) and/or any other suitable solutions and materials, such as those used in processing the buoyant particles (e.g., materials of $1^{st}$ layer, materials of $2^{nd}$ layer, materials of $3^{rd}$ layer, buffers, reagents, etc.). The reaction vessel 110 can receive the set of buoyant particles from any or all of: a user (e.g., user dispensing input buoyant particles into the reaction vessel), a reservoir (e.g., through an automated mechanism such as an automated circulation subsystem of the system), another component of the system (e.g., from a filter through a set of fluid pathways as described below), and/or from other suitable individual or system component. In some variations, the set of input buoyant particles are received into a cavity of the reaction vessel from a first source (e.g., user, chamber, etc.) and subsequently received after each of a set of processing steps from another component of the system (e.g., through a set of pathways in a closed system).

The reaction vessel can receive any number of solutions (e.g., buffer solutions includes at least one of PBS, BSA, and/or EDTA), which can include any suitable reagents, growth factors, chemical compounds, solvents, and/or be of any suitable pH, temperature, or other characteristic to support the viability of buoyant particles (e.g., minimize particle aggregation, improve long-term storage, etc.), processing materials, and/or target constituents.

The reaction vessel 110 is preferably made of glass but can additionally or alternatively be made of a polymer (e.g., plastic), metal, wood, or any other suitable material. The reaction vessel preferably defines a single cavity, such that the set of buoyant particles are processed in the same environment, but can additionally define multiple cavities (e.g., to scale up a method as described below). Furthermore, any surface (exterior and/or interior) of the reaction vessel 110 can be optionally treated with a surface coating (e.g., to influence surface properties, adhesion properties, optical properties, to prevent adhesion of the set of buoyant particles to an inner surface of the reaction vessel, etc.).

The reaction vessel 110 can include and/or define a set of one or more inlets 112, which function to receive any or all of: the set of buoyant particles (e.g., the input set of buoyant particles, buoyant particles having one or more surface modifications, etc.), buffers (e.g., wash buffers), reagents, processing materials (e.g., $1^{st}$ layer materials, $2^{nd}$ layer materials, $3^{rd}$ layer materials, etc.), a stirring subsystem (e.g., as described below), and/or any other suitable materials. The set of inlets 112 preferably includes multiple inlets (e.g., each configured to receive a different material), further preferably a set of inlets arranged on a superior (e.g., top) surface of the reaction vessel 110, but can additionally or alternatively include a single inlet and/or a set of inlets arranged at any suitable surface of the reaction vessel 110. In one variation (e.g., as shown in FIG. 9), the reaction vessel 110 includes a first inlet configured to receive a wash buffer (e.g., from a wash buffer chamber), a second inlet configured to receive a set and/or sets of processing materials (e.g., $1^{st}$ layer materials, $2^{nd}$ layer materials, $3^{rd}$ layer materials, etching materials, etc.), and a third inlet configured to receive the buoyant particles (e.g., from a filter as described below) after one or more surface modification processes and/or washes.

The reaction vessel 110 can additionally include and/or define a set of one or more outlets 114, which functions to remove any or all of the contents of the reaction vessel 110 (e.g., after a surface modification process, after a wash, etc.). The reaction vessel 110 preferably includes a single outlet 114 arranged on an inferior (e.g., bottom) surface of the reaction vessel 110, but can additionally or alternatively include a single outlet and/or multiple outlets arranged on any suitable surface of the reaction vessel. In one variation (e.g., as shown in FIG. 9), the reaction vessel 110 includes an outlet configured to remove the contents of the reaction vessel 110 (e.g., which are next transported to a feed inlet of the filter) after a surface modification process such that the reaction vessel 110 can be prepared with new materials (e.g., from any or all of the set of inlets described above) for a subsequent process.

The reaction vessel can optionally include and/or be configured to interface with any or all of: a set of reservoirs and/or chambers containing one or more materials (e.g., buffers, solutions, wash buffer, surface modification materials, layer materials, buoyant particles, etc.); a heating and/or cooling subsystem (e.g., to achieve and/or maintain a temperature required for processing the buoyant particles); a sensor system (e.g., temperature sensor, pressure sensor, flow rate sensor, etc.); and/or any other suitable component(s) configured to enable a processing of the set of buoyant particles.

Figure 9:
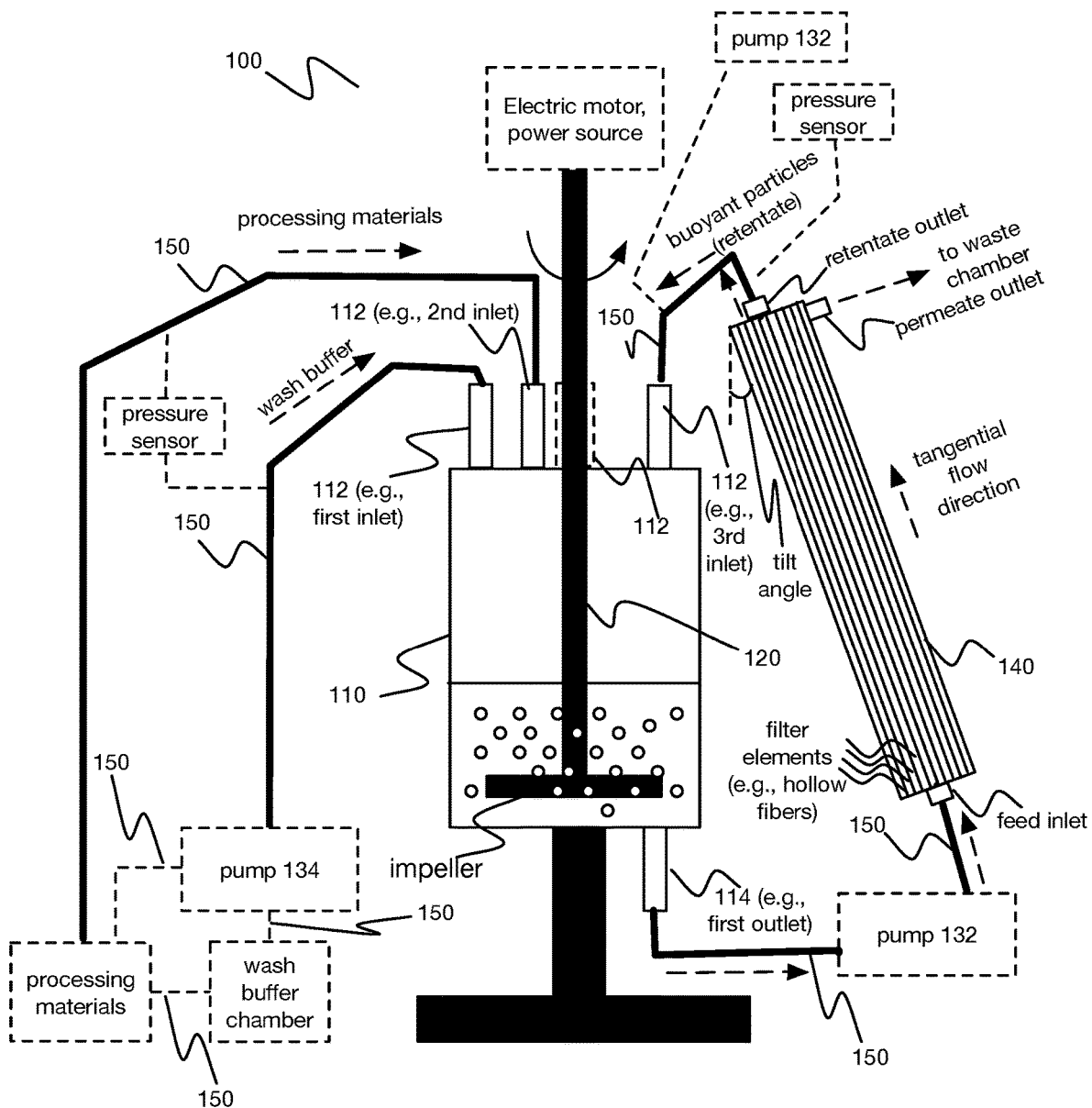
FIG. 9 depicts a variation of the system 100 for buoyant particle processing.

In a first variation (e.g., as shown in FIG. 9), the reaction vessel includes a $1^{st}$ inlet configured to receive (e.g., fluidly connected to) a wash buffer (e.g., from a wash buffer reservoir), a $2^{nd}$ inlet configured to receive a set of processing materials, a $3^{rd}$ inlet to receive the set of buoyant particles (e.g., after being filtered), and an outlet configured to receive the contents of the reaction vessel (e.g., and pass them through a filter using a pump). Additionally or alternatively, the system can include any or all of: a $4^{th}$ inlet configured to receive a stirring mechanism, multiple outlets, any number of additional inlets, and/or any other suitable components.

3.2 System: Stirring Mechanism 120

The system 100 includes a stirring mechanism 120, which functions to constantly and consistently circulate the set of buoyant particles, which can in turn function to prevent and/or minimize clogging of one or more system components, to prevent the buoyant particles from floating and aggregating at the top of the reaction vessel (e.g., thereby experiencing an overall uneven coating of processing materials). Additionally or alternatively, the stirring mechanism 120 can function to mix a set of buoyant particles with a set of processing materials (e.g., to ensure even and thorough coating of buoyant particles with a set of surface layers), perform the method in absence of centrifugation (e.g., as performed in conventional buoyant particle processing, as performed in small-scale buoyant particle processing, etc.), and/or perform any other suitable function.

The stirring mechanism 120 preferably includes an impeller arranged in a cavity of the reaction vessel (e.g., such that the impeller is fully submerged by a processing solution, proximal to a bottom surface defining the internal cavity, etc.) and a motor (e.g., electric motor) configured to rotate the impeller. The stirring mechanism 120 can additionally or alternatively include and/or be configured to interface with any or all of: a power source (e.g., battery, wall outlet, etc.) configured to power the electric motor, a rod (e.g., a stir rod, rod connecting the motor to the impeller, etc.), any suitable stirring device (e.g., fanned rod, magnetic stir bar, etc.), and/or any other stirring device.

The stirring mechanism 120 is preferably operated without or with minimal user intervention (e.g., turned "on" and "off" by a user) but can additionally or alternatively be manually operated. The stirring mechanism 120 preferably stirs the contents of the reaction vessel at a speed fast enough to maintain an approximately uniform spacing between the buoyant particles, such that each buoyant particle is coated with the processing materials, yet slow enough to prevent and/or minimize a breakage of the buoyant particles. Additionally or alternatively, the impeller can rotate at any suitable speed(s).

In a first variation of the stirring mechanism 120, the stirring mechanism 120 includes an impeller arranged proximal to a bottom surface defining an internal cavity of the reaction vessel, wherein the impeller is rotated by an electric motor arranged above the reaction vessel and coupled to a power source (e.g., battery, wall outlet, etc.). In a specific example of this variation, the angular speed of the impeller is between 2400 and 3000°/s (and/or between 400 and 500 rpm). Additionally or alternatively, an angular speed of the impeller can be less than 2400°/s, greater than 3000°/s, less than 400 rpm, greater than 500 rpm, and/or have any other suitable value or range of values.

3.3 System: Set of Pumps 130

The system 100 includes a set of one or more pumps 130, which can individually and/or collectively function to transport any or all of: the set of buoyant particles, one or more solutions (e.g., buffers, reagents, etc.), processing materials, and/or any other material(s) throughout the system 100 (e.g., within components, between components, into the system, out of the system, etc.). One or more of the set of pumps 130 further preferably functions to prevent and/or minimize breakage of the set of buoyant particles, but the set of pumps 130 can additionally or alternatively perform any other suitable function.

The set of pumps 130 includes a first pump 132, which is arranged downstream of an outlet of the reaction vessel 110 and upstream of a filter (e.g., as described below). The first pump 132 is preferably connected through a fluidic pathway (e.g., tubing) to an outlet (e.g., inferior outlet) of the reaction vessel 110, but can additionally or alternatively be coupled to the reaction vessel 110 in any other suitable way. The first pump 132 functions to transport the set of buoyant particles from the reaction vessel 110 to the filter and to prevent and/or minimize breakage of the set of buoyant particles during transport. The first pump 132 preferably includes a diaphragm pump (e.g., 4-piston diaphragm pump, 2-piston diaphragm pump, etc.), wherein the diaphragm pump enables minimal contact (e.g., in comparison with another type of pump, in comparison with a peristaltic pump, etc.) and minimal associated contact forces (e.g., contact force large enough to break a buoyant particle) between the pump and the particles. Additionally, the diaphragm pump can enable minimal contact and minimal associated contact forces between adjacent particles (e.g., when restricted in a small diameter passageway of a peristaltic pump).

The first pump 132 is preferably operated in accordance with a flow rate configured to minimize breakage of buoyant particles. The flow rate of the first pump 132 (and/or a second pump 134) is further preferably determined based on any or all of: a total length of the system (e.g., distance particle traverses from the reaction vessel to the filter and back to the reaction vessel), a timing of one or more processes of the method (e.g., time required to add a new set of inputs to the reaction vessel such that the buoyant particles aren't placed into an empty reaction vessel, etc.). In a variation, the first pump 132 is operated with a flow rate between 400 mL/min and 600 mL/min. Additionally or alternatively, the first pump 132 can be operated with a flow rate between 200 mL/min and 1000 mL/min, with a flow rate less than 400 mL/min, with a flow rate greater than 600 mL/min, and/or in accordance with any suitable operating parameters having any suitable values.

The set of pumps 130 preferably includes a second pump 134, wherein the second pump 134 functions to pump one or more fluids (e.g., buffers, solvents, washes, etc.) into the reaction vessel 110. The second pump 134 preferably does not interact with the set of buoyant particles, but can additionally or alternatively pump buoyant particles into the reaction vessel, remove any suitable materials from the reaction vessel 110, transport one or more solutions between components of the system, or otherwise interact with any suitable materials of the system 100. The second pump 134 is preferably arranged upstream of the reaction vessel 110 and connected to the reaction vessel through a fluidic pathway (e.g., flexible tube) connected to a superior inlet of the reaction vessel 110. Additionally or alternatively, the second pump 134 can be arranged downstream of a wash buffer chamber (e.g., and configured to pump fresh wash buffer into the system during washes), a container holding a set of processing materials, and/or any other solutions and materials to be added to the reaction vessel 110. The second pump 134 can be a different pump type (e.g., peristaltic pump) than the first pump, the same pump type (e.g., diaphragm pump), or any other suitable pump type.

The set of pumps 130 can additionally or alternatively include a single pump, additional pumps, a different pump type, or any other suitable pumps in any suitable arrangement.

In one variation of the set of pumps 130 (e.g., as shown in FIG. 9), the set of pumps includes a first pump 132 arranged between an outlet of the reaction vessel 100 and an inlet of a filter 140, and a second pump 134 arranged between a wash buffer chamber and the reaction vessel 110. In a specific example, the first pump 132 is a diaphragm pump (e.g., quaternary diaphragm pump) configured to gently transport a set of buoyant particles from the reaction vessel 110 to the filter 140, and wherein the second pump 134 is a peristaltic pump configured to pump wash buffer into and/or throughout the system (e.g., into the reaction vessel) during washes (e.g., in-between particle processing steps).

3.4 System: Filter 140

The system includes a filter 140, which functions to separate the set of buoyant particles from waste materials (e.g., wash buffers, processing materials, debris, etc.) after one or more buoyant particle processing processes. Additionally or alternatively, the filter 140 can function to separate the set of buoyant particles from any other solutions and materials (e.g., separate from a storage buffer prior to a first processing process); prevent and/or minimize a clogging of one or more components of the system (e.g., materials with highest buoyancy pass through the filter whereas other materials are collected in the filter); directly collect buoyant particles (e.g., from an outlet of the filter); enable a fast washing (e.g., less than 10 minutes, less than 5 minutes, between 5 seconds and 2 minutes, less than 5 seconds, etc.) of buoyant particles; and/or perform any other suitable function.

Further additionally or alternatively, the filter 140 can function to enable large volume buoyant particle processing relative to conventional processing protocols (e.g., including centrifugation, including manual processing and/or preparation, etc.). In some conventional processing methods, for instance, a set of centrifugation processes are required to separate the set of buoyant particles from surrounding solutions and materials. Conventional processing methods can require, for instance, any or all of: limited-volume, batched separation (e.g., based on centrifuge tube volumes); user intervention (e.g., to operate the centrifuge, to pipette the buoyant particles into and/or out of centrifuge tubes, to place and/or remove centrifuge tubes from the centrifuge, etc.); removal of the buoyant particles from a system (e.g., a closed system, a reaction vessel, etc.); and/or any other requirements. The filter 140 preferably functions to eliminate and/or minimize one or more of these requirements, but can additionally or alternatively eliminate and/or minimize another requirement, have one or more of these requirements (e.g., be used in conjunction with a centrifuge, etc.), or perform any other suitable function.

The filter 140 preferably separates the set of buoyant particles from a surrounding solution, wherein the surrounding solution includes any or all of: one or more processing materials (e.g., $1^{st}$ layer elements, $2^{nd}$ layer elements, $3^{rd}$ layer elements, etc.); one or more fluids such as buffers, solvents, other solutions in the reaction vessel 110; debris (e.g., broken buoyant particles); and/or any other suitable materials. The buoyant particles are preferably separated from a surrounding solution after each particle processing process (e.g., and prior to a subsequent processing process), but can additionally or alternatively be separated from a surrounding solution prior to a processing process (e.g., to filter out a storage buffer); be separated from a second set of buoyant particles (e.g., based on size such that the set of buoyant particles are uniformly sized); and/or be otherwise separated from any suitable material.

Figure 7:
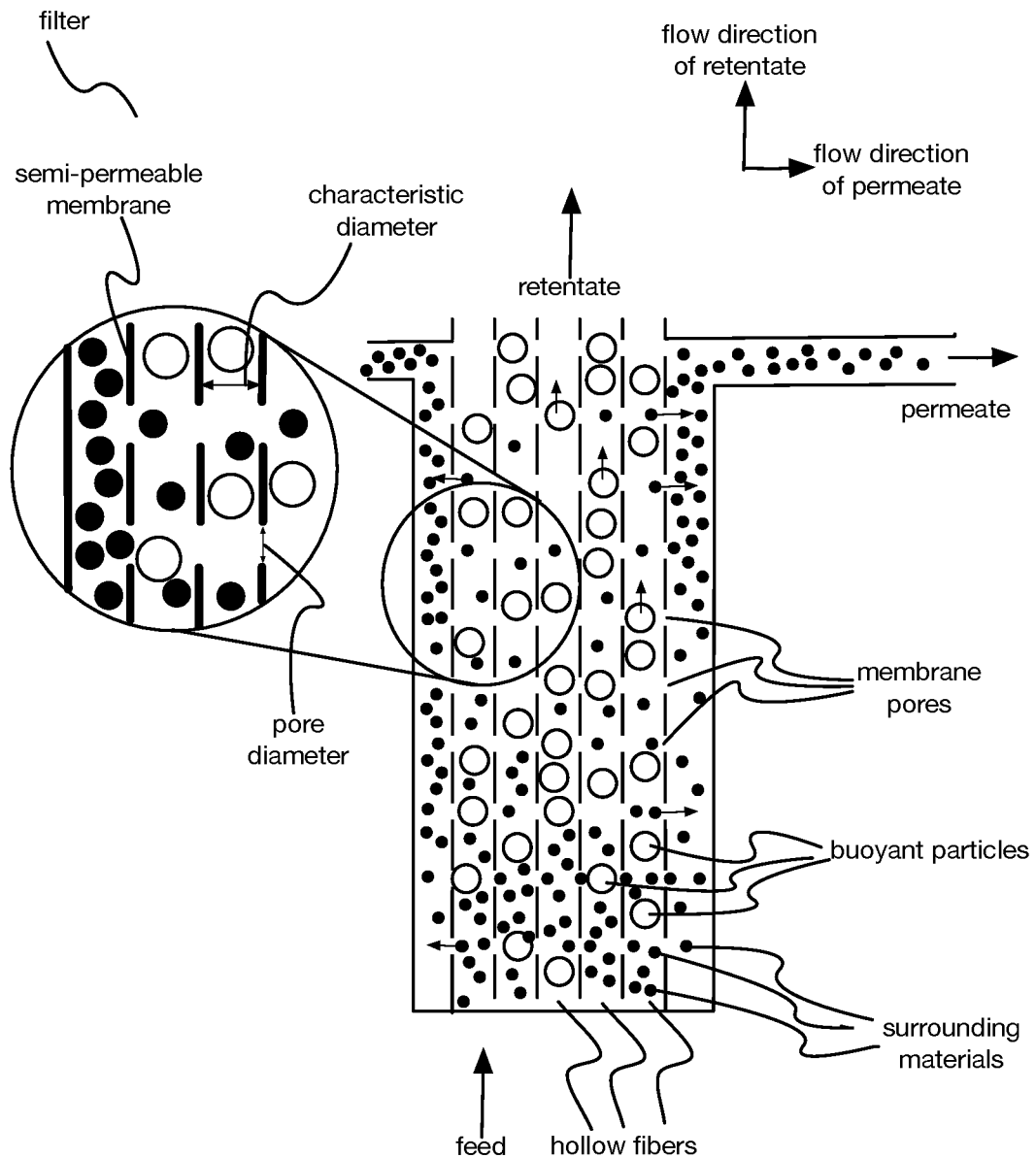
FIG. 7 depicts a cross-sectional view of a variation of a tangential flow filter.

The filter 140 preferably includes a tangential flow filter (e.g., hollow fiber membrane filter), wherein the set of buoyant particles (which form the retentate) are retained within the membrane (e.g., semi-permeable membrane, wall, barrier, inner wall, inner diameter, outer wall, outer diameter, etc.) of (e.g., based on buoyancy, based on size, based on buoyancy and size, etc.) a set of filter elements (e.g., columns, fibers, plate having apertures, mesh, etc.), and wherein part or all of the remaining solution (e.g., permeate) passes through the set of filter elements (e.g., tangential to the flow of the feed channel/retentate, non-parallel with respect to a central axis of each filter element, perpendicular to a central axis of each filter element, due to cross flow, etc.). The flow direction of the buoyant particles (which form the retentate) within the filter membrane(s) is non-parallel (e.g., perpendicular, approximately perpendicular, at an angle between 70 and 100 degrees, etc.) with respect to the flow direction of the remaining solution (which forms the permeate) through the membrane (e.g., as shown in FIG. 7). In preferred variations of the filter 140, for instance, the filter 140 has a nonzero angle (e.g., 90 degrees, 45 degrees, between 45 and 90 degrees, less than 45 degrees, greater than 90 degrees, etc.) between a flow direction of the feed/retentate (e.g., central axis of the filter element) and a flow direction of the permeate.

Figure 8:
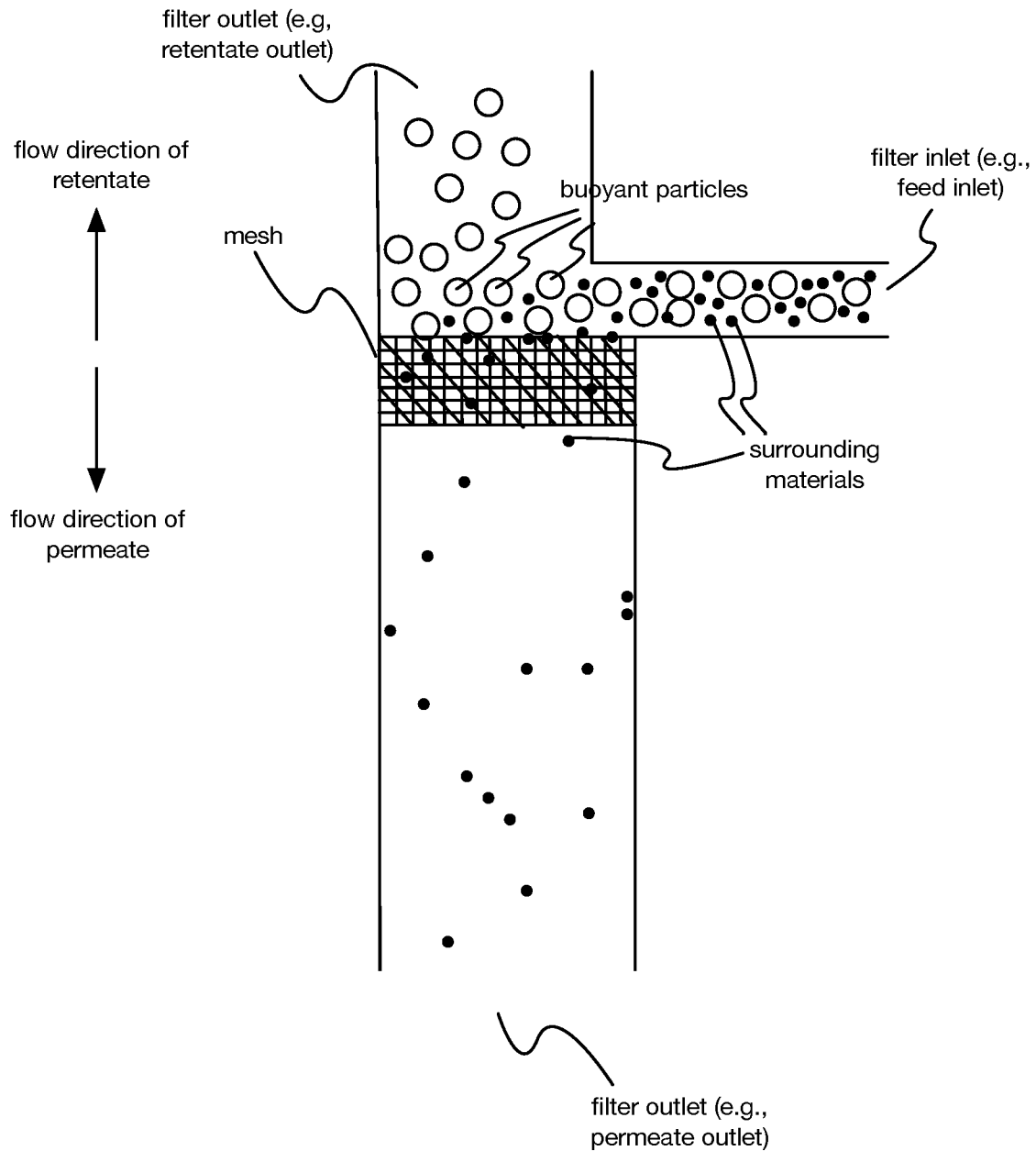
FIG. 8 depicts a cross-sectional view of a variation of a direct flow filter.

Additionally or alternatively, the filter 140 can include a direct flow filter (e.g., mesh filter, fret filter, filter as shown in FIG. 8, etc.), wherein an inlet of the filter is arranged perpendicular to a flow direction (e.g., direction of a central axis) within the filter elements.

The filter 140 can optionally be a gravity-assisted filter (e.g., direct flow filter, filter wherein the flow direction of the remaining solution through the filter is aligned or at least partially aligned with gravity, etc.), but can additionally or alternatively be assisted with a pump (e.g., first pump 132), an attractive mechanism (e.g., magnet arranged downstream of a filter element to attract magnetic particles), unassisted, and/or otherwise assisted.

In a first variation (e.g., as shown in FIG. 7), the filter 140 is a tangential flow filter arranged in a vertical (e.g., along the direction of gravity) or partially vertical (e.g., near vertical, non-horizontal, etc.) alignment with respect to gravity, wherein a feed inlet of the filter 140 is parallel with a retentate outlet of the filter 140, wherein the set of buoyant particles travel from the feed inlet to the retentate outlet within a set of hollow fiber filter elements along a direction aligned with the central axis of each hollow fiber. A permeate outlet of the filter 140 is arranged perpendicular to both the feed inlet and the retentate outlet, wherein the permeate (e.g., remaining solution) exits through the semi-permeable membranes of each filter element (e.g., through cross flow) and exits the filter at a flow direction perpendicular to the central axis of the filter elements (e.g., the retentate flow direction, and feed flow direction, the retentate and feed flow directions, etc.).

In a second variation (e.g., as shown in FIG. 8), the filter 140 is a direct flow filter arranged in a vertical (e.g., along the direction of gravity) or partially vertical (e.g., near vertical, non-horizontal, etc.) alignment with an inlet arranged perpendicular to this (e.g., horizontal, near horizontal, etc.). An outlet of the filter can be arranged perpendicular to the inlet (e.g., to leverage a buoyancy of the buoyant particles, with the assistance of a pump, etc.), parallel to the inlet (e.g., as shown in FIG. 8), and/or at any suitable angle with respect to the inlet (e.g., between 0 and 90 degrees, greater than 90 degrees, etc.). Additionally or alternatively, the filter 140 can be arranged in any suitable orientation with any suitable angles between filter subcomponents. In variations of the direct flow filter, the flow directions of the retentate and the permeate are preferably parallel (e.g., retentate flow direction is parallel with the permeate flow direction in FIG. 8). Alternatively, the flow directions of the retentate and permeate can be arranged with any suitable angle respect to each other (e.g., 45 degrees, 90 degrees, between 160 and 200 degrees, less than 180 degrees, greater than 180 degrees, etc.). In a set of specific examples, the filter 140 is arranged with a nonzero tilt angle, such that the set of buoyant particles are directed toward an outlet of the filter (e.g., arranged on a superior surface (top) of the filter).

The filter 140 is preferably arranged downstream of the reaction vessel 110, further preferably additionally downstream of a first pump 132, and upstream of an inlet of the reaction vessel 110, such that the filter 140 receives the contents of the reaction vessel 110 (e.g., after a particle processing process), which can be optionally brought to an inlet of the filter through the pump 132 (e.g., via a set of fluidic pathways). Additionally or alternatively, the filter 140 can be arranged with respect to other components of the system 100 in any suitable way.

Each filter element (e.g., channel, hollow fiber, tube, cylinder, aperture in a direct flow filter, pore in a direct flow filter, frit in a direct flow filter, etc.) of the filter preferably has a cross section with a characteristic diameter (e.g., inner diameter, outer diameter, inner diameter of a hollow fiber, etc.) larger than the diameter of each buoyant particle (e.g., in a transverse flow filter), wherein the characteristic diameter defines an upper limit of a size range of particles which can enter the filter elements, such that the buoyant particles can enter the filter elements (e.g., travel along a length of a hollow fiber, pass through an aperture, enter an inner lumen of a filter element, etc.). The characteristic diameter of each filter element is further preferably larger than the surrounding material (e.g., processing materials, debris, etc.) to be separated from the buoyant particles, such that the surrounding materials can also enter the filter elements. Additionally or alternatively, any or all of the filter elements can have a characteristic diameter smaller than at least a partial set of the buoyant particles (e.g., to filter the buoyant particles by size, in a direct flow filter, etc.), a variable diameter (e.g., range of diameters among the filter elements), and/or any other suitable dimensions. The filter elements are preferably identical (e.g., have the same diameter, have the same dimensions, etc.), but can additionally or alternatively have variation (e.g., an increasing diameter from upstream to downstream filter elements such that the surrounding material to be separated from the buoyant particles is sorted by size).

In some variations (e.g., wherein each buoyant particle is a microbubble), a characteristic diameter of each filter element (e.g., each hollow fiber in a hollow fiber filter) is greater than 10 microns and less than 10,000 microns (e.g., between 100 and 1000 microns, greater than 30 microns, less than 100 microns, greater than 100 microns, etc.). Additionally or alternatively, the filter elements can have various diameters (e.g., each greater than 10 microns, each between 100 and 1000 microns, each between 10 and 30 microns, etc.), or any other suitable diameter(s).

Each filter element further preferably includes and/or defines (e.g., in the case of a tangential flow filter) a semi-permeable membrane having a set of membrane pores, which function to separate (filter) one or more surrounding materials (e.g., through cross flow) from the buoyant particles which remain within the membrane of the filter element. A diameter of each of the set of membrane pores is preferably smaller than a diameter of the buoyant particle and larger than a diameter than any or all of the components in the remaining solution (permeate). The membrane pores define a central axis arranged in a non-parallel (e.g., perpendicular, substantially perpendicular, at an angle between 80 and 100 degrees, etc.) orientation with respect to a central axis of the filter element (e.g., defining the characteristic diameter, inner diameter of a hollow fiber, etc.). As such, the membrane pores function to prevent buoyant particles from exiting through the semi-permeable membrane while enabling the surrounding material (e.g., all of the surrounding material, a portion of the surrounding material, etc.) to exit the filter element through the semi-permeable membrane (e.g., through cross flow).

In some variations, the diameter of at least each of a partial set of membrane pores is less than 10 microns (e.g., 0.2 microns, 0.5 microns, between 0.1 and 1 microns, greater than 1 micron, etc.), but can additionally or alternatively be less than 30 microns, greater than 10 microns, between 10 and 100 microns, or have any other suitable diameter.

The length of the filter (e.g., length of each hollow fiber module) as measured in the direction of flow of the materials being collected by and/or within the filter elements can have any suitable value (e.g., greater than 12 inches, less than 12 inches, between 4 inches and 18 inches, between 10 inches and 30 inches, greater than 30 inches, less than 60 inches, etc.). The number of filter elements (e.g., hollow fibers, pores, etc.) in the filter is preferably configured to enable a large-scale processing (e.g., enable a predetermined flow rate, enable a predetermined reaction vessel volume, enable a predetermined total processing time, etc.) of buoyant particles (e.g., without clogging the filter) but can additionally or alternatively configured.

For the set of filter elements (e.g., hollow fibers), there can be a nonzero spacing between adjacent filter elements, can be in contact along a partial length of adjacent filter elements, can be in contact along a full length of adjacent filter elements, or otherwise arranged.

The filter can additionally include one or more ports, such as a port for adjusting pressure in the filter, which can function to: keep the solution flowing through the filter, assist and/or enable the set of buoyant particles (e.g., retentate) to exit the filter (e.g., and re-enter the reaction vessel), assist and/or enable the surrounding materials (e.g., permeate) to pass through the filter elements (e.g., traverse a length of a hollow fiber module), unclog the filter, and/or perform any other suitable function.

The filter element preferably includes one or more plastic materials in the semi-permeable membrane, which define a set of membrane pores through which the surrounding materials exit the filter elements. Additionally or alternatively, the filter elements can include any or all of: a polymer, glass, wood, metal, natural fiber, synthetic fiber, fabric, ceramic, and/or any other suitable material(s).

In one variation, the filter 140 includes a hollow fiber tangential filter, wherein the hollow fiber filter includes a bundle of hollow fibers (e.g., closely packed, with negligible gaps between adjacent hollow fibers, etc.). The hollow fiber filter receives the set of buoyant particles along with the surrounding solution (e.g., after a particle processing process, after a wash step, etc.) from the reaction vessel 110 (e.g., after being passed through a first pump 132) and separates the set of buoyant particles (e.g., retentate) from the surrounding solution (e.g., wash buffer and debris), wherein the set of buoyant particles, which form the retentate, flows through the hollow fibers (e.g., in a direction parallel with a central axis of the hollow fibers) and exits through an outlet (e.g., and back into the reaction vessel 110, into a separate container, etc.) whereas the surrounding solution, which forms the permeate, exits the hollow fibers through a set of fiber membrane pores (e.g., in a semipermeable membrane) in a cross flow direction, wherein the cross flow direction is perpendicular to the retentate flow direction. The permeate can then optionally be collected at a waste chamber.

3.5 System: Set of Pathways 150

The system 100 includes a set of pathways 150, which can include any number of tubes (e.g., flexible tubes), channels, conduits, columns, and/or any other suitable pathways configured to transport the set of buoyant particles (e.g., and any surrounding solution) throughout the system 100. The set of pathways 150 further preferably functions to connect multiple components of the system together (e.g., to create a closed system), consistently and constantly circulate the inputs of the system (e.g., to prevent clogging), and/or perform any other suitable function.

The set of pathways 150 can include and/or define any or all of: a set of ports (e.g., to regulate a pressure within any or all of the system), a set of inlets, a set of outlets, a surface coating and/or surface modifications (e.g., to reduce friction within an inner lumen of a pathway, to prevent attraction between the set of buoyant particles and an inner lumen of the pathway, etc.), and/or any other suitable features.

In one variation, the set of pathways 150 includes a set of flexible tubes which connect adjacent components of the system 100 together, through which any or all of: the set of buoyant particles, buffers, processing materials, debris, reagents, and/or other solutions and materials circulate.

3.6 System: Additional Components

The system 100 can additionally or alternatively include any or all of: a set of sensors, such as a pressure sensor (e.g., a pressure sensor to measure an internal pressure of a closed system 100, a pressure sensor to measure a pressure within a fluidic pathway, etc.), a temperature sensor (e.g., to maintain a predetermined temperature or range of temperatures for buoyant particle processing), a flow rate sensor, and/or any other suitable sensor(s); a control subsystem (e.g., processing subsystem, processor, controller, etc.); a power source (e.g., to power the stirring mechanism, to power one or more pumps, etc.); and/or any other suitable component(s).

3.7 System: Variations

In one variation of the system 100 (e.g., as shown in FIG. 9), the system 100 includes: a reaction vessel 110, wherein the reaction vessel 110 functions to receive a set of buoyant particles (e.g., microbubbles), a set of processing materials (e.g., $1^{st}$ layer materials, $2^{nd}$ layer materials, $3^{rd}$ layer materials, etc.), and any additional solutions (e.g., buffers) or materials, wherein the set of buoyant particles are at least partially processed within the reaction vessel 110; a stirring mechanism 120 including an impeller arranged within a cavity of the reaction vessel 110; a stir rod connected to the impeller; and an electric motor arranged above the reaction vessel 110 and configured to rotate the stir rod; a first pump 132 (e.g., a quaternary diaphragm pump), wherein the first pump 132 is configured to transport (e.g., gently transport, transport with minimal breakage of the set of buoyant particles, etc.) the set of buoyant particles (e.g., and other contents of the reaction vessel 110) to a tangential flow filter 140 (e.g., hollow fiber filter), wherein the filter 140 collects (e.g., and collects at a waste chamber) solutions and materials excluding the set of buoyant particles through a set of membrane pores of the filter elements (e.g., hollow fibers having an inner diameter larger than a diameter of each of the buoyant particles and a set of membrane pores with a diameter smaller than a diameter of each of the set of buoyant particles but larger than a diameter of the components of the surrounding solution) and outputs the set of buoyant particles through a retentate outlet of the filter; and a set of fluidic pathways 150 which circulate the inputs of the system 100 (e.g., the set of buoyant particles, solutions, processing materials, etc.) from the reaction vessel 110 to the filter 140 and back to the reaction vessel 110 or final collection container (e.g., after all processing processes have been completed). The system 100 can additionally include any or all of: a first pump 130 (e.g., a peristaltic pump) configured to add one or more inputs (e.g., wash buffer) into the reaction vessel 110; a set of pressure sensors (e.g., to monitor a pressure in one or more fluidic pathways, to monitor a pressure in the filter, to monitor a pressure in the reaction vessel 110, etc.), and/or any other suitable components.

4. Method 200

The method 200 for buoyant particle processing functions to apply one or more surface modifications to a set of buoyant particles. Additionally or alternatively, the method 200 can function to wash a set of buoyant particles, filter a set of buoyant particles (e.g., from broken particle fragments, debris, particles having a different size, etc.), prevent breakage of a set of particles, operate a closed system with minimal and/or no user intervention, and/or perform any other suitable function.

The method 200 is preferably performed with a system 100 as described above but can additionally or alternatively be performed with any suitable system.

4.1 Method: Preprocessing a set of Buoyant Particles S210

The method 200 can optionally include preprocessing the set of buoyant particles S210 (e.g., prior to an application of a first layer), which functions to prepare the set of buoyant particles S210 for any or all of the subsequent processes (e.g., application of a first layer) of the method 200. S210 can include any or all of: the application of a surface layer (e.g., protective surface layer, protective shell to prevent leaching, adhesion-promoting surface layer, etc.), the modification of a buoyant particle surface (e.g., etching, increasing surface roughness, etc.), or any other suitable process.

S210 is preferably performed first in the method 200 but can additionally or alternatively be performed multiple times throughout the method 200, later in the method 200 (e.g., after washing, after filtering, after filtering for size, etc.), not performed at all, or otherwise performed at any suitable time(s).

S210 can be performed within a system 100 (e.g., in a reaction vessel 110), outside of the system 100 (e.g., at a microbubble manufacturing facility, at a lab bench, etc.), or at any other suitable location.

In one variation, the method 200 includes S210, wherein S210 is performed prior to the application of a first layer (e.g., prior to S220, prior to S230, prior to S240, etc.). In a specific example, S210 includes the addition of aminosilane groups to surface (e.g., raw glass surface) of a set of buoyant particles through incubating the set of buoyant particles with a solvent, wherein the set of buoyant particles are dried prior to being introduced into the system (e.g., system 100).

4.2 Method: Adding a Set of Inputs to a Reaction Vessel S220

The method 200 can optionally include adding a set of inputs to a reaction vessel S220, which functions to initiate one or more future processes of the method 200.

The set of inputs preferably includes the set of buoyant particles and any other inputs required for processing, maintaining, and/or washing the set of buoyant particles, such as any or all of: buffers (e.g., storage buffer, wash buffer, etc.), processing materials (e.g., $1^{st}$ layer materials, $2^{nd}$ layer materials, $3^{rd}$ layer materials, etc.), other fluids and/or solutions (e.g., required to enable a reaction between the set of buoyant particles and the processing materials, water, solvents, reagents, etc.), and/or any other suitable solutions and materials.

The set of inputs can be added to the reaction vessel through and/or from any or all of: a user (e.g., by a user, by a user pipetting a set of inputs into the reaction vessel, by a user pouring a set of inputs into the reaction vessel, etc.), a component of the system 100 (e.g., a container via a pump and a fluidic pathway, a fluidic pathway, a filter, etc.), and/or any other suitable source. The set of inputs can be added to the reaction vessel manually, automatically, or any combination of both. The set of inputs can be added to the reaction vessel separately (e.g., at multiple times, one at a time, $2^{nd}$ layer materials added after set of buoyant particles re-enters the reaction vessel from a filter, $3^{rd}$ layer materials added after set of buoyant particles re-enters the filter a second time, etc.), simultaneously, or any combination of both.

Adding a set of processing materials to the reaction vessel can include adding materials corresponding to one or more layers (e.g., first layer, second layer, third layer, etc.) to the reaction vessel. Preferably, materials are added a single layer at a time (e.g., first layer processing materials added at a first time, second layer processing materials added at a second time after the $1^{st}$ layer has been formed, etc.), which can function to promote an ordered, sequential layering to the set of buoyant particles, which can in turn function to prevent nonspecific binding. The inputs are preferably added to the reaction vessel through one or more inlet ports, but can additionally or alternatively be added in any suitable way.

S220 can optionally be followed by a waiting time, which functions to enable the processing materials to completely and evenly coat the buoyant particles. The waiting time preferably occurs while the contents of the reaction vessel are being stirred but can additionally or alternatively be performed in the absence of stirring, in the presence of heating, in the presence or cooling, and/or in any other environment. In some variations, for instance, the processing of the buoyant particles (e.g., addition of a single layer) is performed for 1 hour (e.g., with stirring).

S220 can be performed a single time (e.g., just $2^{nd}$ layer, just $3^{rd}$ layer, etc.) or multiple times (e.g., $2^{nd}$ layer followed by $3^{rd}$ layer, $1^{st}$ layer followed by $2^{nd}$ layer, $1^{st}$ layer followed by $2^{nd}$ layer followed by $3^{rd}$ layer, etc.) throughout the method 200.

In one variation, S220 includes adding a set of buoyant particles with a first set of processing materials (e.g., and any accompanying solutions) to the reaction vessel 110 at a first time; adding the filtered set of buoyant particles having a $1^{st}$ layer (e.g., via the filter) and a second set of processing materials (e.g., manually by a user) to the reaction vessel at a second time; and adding the filtered set of buoyant particles having a $1^{st}$ layer and a $2^{nd}$ layer, and a third set of processing materials to the reaction vessel at a third time.

4.3 Method: Stirring the Contents of the Reaction Vessel S230

The method includes stirring the contents (e.g., inputs) of the reaction vessel S230 (e.g., with a stirring mechanism 120), which functions to fully suspend the set of buoyant particles and promote a uniform coating of the buoyant particles with the processing materials. S230 is preferably performed throughout (e.g., continuously) subsequent processes the method 200, but can additionally or alternatively be performed throughout the entire method 200 (e.g., during preprocessing), intermittently (e.g., at predetermined times, at random times, upon detecting a non-zero volume within the reaction vessel, etc.), or at any suitable time(s).

S230 is preferably performed in accordance with a set of stir parameters (e.g., rotational velocity, rotational acceleration, etc.) configured to maintain and/or enable any or all of: a constant motion of each of the set of buoyant particles, a spacing between buoyant particles above a predetermined threshold (e.g., greater than 0.1 microns, greater than 0.5 microns, greater than 5 microns, greater than 10 microns, etc.), a distribution of buoyant particles (e.g., even distribution, somewhat uneven distribution, presence of buoyant particles below a surface of the volume in the reaction vessel, presence of buoyant particles below a middle height of the volume in the reaction vessel, etc.), an even coating of each of the set of buoyant particles (e.g., between 75% and 100% of buoyant particles are properly coated, greater than 50% of buoyant particles are properly coated, etc.), and/or be otherwise configured. One or more stir parameters can additionally or alternatively be determined based on any or all of: the particular set of processing materials in the reaction vessel, a time (e.g., a time required for buoyant particles to circulate through system, etc.), a pump parameter, a height of the reaction vessel, and/or any other suitable parameters.

In one variation, the contents of the reaction vessel are constantly stirred throughout the method by a stirring mechanism, wherein the stirring mechanism rotates at a speed between 400 and 500 rpm. Additionally or alternatively, the stirring mechanism can rotate at a speed less than 400 rpm, greater than 500 rpm, and/or any other suitable rotational speed.

4.4 Method: Washing the Set of Buoyant Particles S240

The method 200 can include washing the set of buoyant particles S240, which functions to prepare the set of buoyant particles for additional processing (e.g., addition of subsequent layer, subsequent processing, subsequent testing, etc.).

S240 is preferably performed after S230 (e.g., after a waiting time of S230), further preferably after each iteration of S230, but can additionally or alternatively be performed after S250, prior to S230, and/or at any other suitable time(s) during the method 200.

S240 is preferably performed in accordance with a pump (e.g., second pump 134), wherein the pump functions to transfer a wash buffer from a wash buffer container to a cavity of the reaction vessel, but can additionally or alternatively be performed manually, with another component (e.g., of the system 100), in absence of a pump, or otherwise performed.

The wash buffer preferably includes phosphate and sodium chloride, but can additionally or alternatively include any suitable solvents, reagents, solutions, detergents, or other suitable components.

In one variation, S240 includes washing the set of buoyant particles after each of a set of layers has been added to the buoyant particles (e.g., and prior to entering the filter).

4.5 Method: Filtering the Contents of the Reaction Vessel S250

The method includes filtering the contents of the reaction vessel S250, which functions to separate the set of buoyant particles from the remaining contents of the reaction vessel (e.g., wash buffer, processing materials, etc.). The remaining contents can include, for instance: remaining (e.g., unattached, extra, etc.) processing materials, such as any or all of: remaining $1^{st}$ layer elements, remaining $2^{nd}$ layer elements (e.g., linker), remaining $3^{rd}$ layer elements, any other suitable layer elements, wash buffer, other buffer, a solvent, debris (e.g., fragments from broken buoyant particles), and/or any other materials. S250 is preferably performed multiple times throughout the method (e.g., after each of a set of processing processes), but can alternatively be performed a single time. S250 can additionally include collecting waste from an outlet (e.g., permeate outlet), such as in a waste chamber arranged above each of a set of filter elements.

In one variation, S250 includes passing the contents of the reaction vessel through a tangential flow filter (e.g., after S240, prior to S240, in absence of S240, etc.). In a specific example, the contents of the reaction vessel are transferred to the filter via a first pump 132.

4.6 Method: Repeating any or all of the Previous Processes

The method can include repeating any or all of the above processes. In one variation, the method 200 includes repeating S220-250 for each of a set of layers and/or other surface modifications to be added to the set of buoyant particles.

4.7 Method: Variations

In one variation, the method 200 includes: preprocessing a set of buoyant particles (e.g., adding an aminosilane layer to the set of buoyant particles and letting the buoyant particles dry); adding the pre-processed set of buoyant particles along with processing materials associated with a $1^{st}$ layer to the reaction vessel; stirring the contents of the reaction vessel for a predetermined waiting period; washing the set of buoyant particles; filtering the set of buoyant particles from the remaining contents of the reaction vessel; transferring the set of buoyant particles having a first layer back to the reaction vessel; adding a set of processing materials associated with a $2^{nd}$ layer to the reaction vessel; stirring the contents of the reaction vessel for a second predetermined waiting period (e.g., the same as the first waiting period, different than the first waiting period, etc.); washing the set of buoyant particles; filtering the set of buoyant particles from the remaining contents of the reaction vessel; transferring the set of buoyant particles having a first layer and a second layer back to the reaction vessel; adding a set of processing materials associated with a $3^{rd}$ layer to the reaction vessel; stirring the contents of the reaction vessel for a predetermined waiting period (e.g., the same as the first waiting period, different than the first waiting period, the same as the second waiting period, different than the second waiting period, etc.); washing the set of buoyant particles; filtering the set of buoyant particles from the remaining contents of the reaction vessel; and collecting the set of buoyant particles having a $1^{st}$, $2^{nd}$, and $3^{rd}$ layer (e.g., at a container).

Additionally or alternatively, the method 200 can include any other suitable processes performed in any suitable order.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The method 100 and/or system 200 of the preferred embodiment can be embodied and/or implemented at least in part as machine configured to receive a computer-readable medium storing computer-readable instructions. The instructions are preferably executed by computer-executable components preferably integrated with the system and one or more portions of the processor and/or analysis engine. The computer-readable medium can be stored in the cloud and/or on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

Although omitted for conciseness, the preferred embodiments include every combination and permutation of the various system and/or method components.

As a person skilled in the art will recognize from the previous detailed description and from the figures and claims, modifications and changes can be made to the preferred embodiments of the invention without departing from the scope of this invention defined in the following claims.

We claim:

1. A method for processing a set of buoyant particles, the method comprising:
   at a reaction vessel, receiving:
      a set of processing materials; and
      the set of buoyant particles;
   with a stirring subsystem, facilitating bonding of the set of processing materials with the set of buoyant particles, thereby forming a set of bound buoyant particles;
   with a tangential flow filter:
      receiving the set of bound buoyant particles from the reaction vessel;
      with a pump, passing the set of bound buoyant particles through the tangential flow filter; and
   receiving the set of bound buoyant particles at the reaction vessel.

2. The method of claim 1, wherein the tangential flow filter comprises a set of hollow fibers, wherein the set of hollow fibers is tilted relative to vertical with a nonzero tilt angle.

3. The method of claim 2, wherein the nonzero tilt angle is configured to direct the set of bound buoyant particles toward an outlet of the tangential flow filter.

4. The method of claim 2, wherein each of the set of buoyant particles has a particle diameter between 10 and 30 microns, and wherein an inner diameter of each of the set of hollow fibers is greater than the particle diameter.

5. The method of claim 1, wherein the set of buoyant particles has an average density less than an average density of the set of set of processing materials.

6. The method of claim 1, wherein the set of processing materials comprises a first subset of processing materials, a second subset of processing materials, and a third subset of processing materials, wherein:
the first subset of processing materials forms a first layer arranged on the set of buoyant particles;
the second subset of processing materials forms a second layer arranged on the first layer; and
the third subset of processing materials forms a third layer arranged on the second layer.

7. The method of claim 6, wherein:
the first layer comprises a hydroxyl group; and
the second layer comprises a chain of repeating glycol units.

8. The method of claim 7, wherein:
the first layer comprises 3-aminopropyltrimethoxysilane and an amino group;
the second layer comprises an amino-reactive group, a polyethylene glycol chain, and a thiol-reactive group; and
the third layer comprises a thiol group.

9. A method for processing a set of buoyant particles, the method comprising:
a) at a reaction vessel receiving:
a set of processing materials configured to bind to the set of buoyant particles; and
the set of buoyant particles;
b) stirring the contents of the reaction vessel;
c) pumping the contents of the reaction vessel to a tangential flow filter;
d) at the tangential flow filter comprising a fourth inlet, a second outlet, and set of hollow fibers, each of the set of hollow fibers having an inner diameter larger than a diameter of the set of buoyant particles:
receiving the contents of the reaction vessel from the first outlet at the fourth inlet; and
separating the set of buoyant particles from a remainder of the contents of the reaction vessel.

10. The method of claim 9, wherein the set of hollow fibers is tilted relative to vertical with a nonzero tilt angle.

11. The method of claim 10, wherein the nonzero tilt angle is configured to direct the set of bound buoyant particles toward an outlet of the tangential flow filter.

12. The method of claim 9, wherein each of the set of buoyant particles has a particle diameter between 10 and 30 microns, and wherein an inner diameter of each of the set of hollow fibers is greater than the particle diameter.

13. The method of claim 9, further comprising (e): repeating (a) through (d) for a second set of processing materials.

14. The method of claim 13, further comprising (f): repeating (a) through (d) for a third set of processing materials.

15. The method of claim 9, wherein stirring the contents of the reaction vessel is configured to facilitate bonding of the set of processing materials with the set of buoyant particles, thereby forming a set of bound buoyant particles.

16. The method of claim 9, wherein the set of buoyant particles has an average density less than an average density of the set of set of processing materials.

17. The method of claim 9, wherein the set of processing materials comprises a first subset of processing materials, a second subset of processing materials, and a third subset of processing materials, wherein:
the first subset of processing materials forms a first layer arranged on the set of buoyant particles;
the second subset of processing materials forms a second layer arranged on the first layer; and
the third subset of processing materials forms a third layer arranged on the second layer.

18. The method of claim 17, wherein:
the first layer comprises a hydroxyl group; and
the second layer comprises a chain of repeating glycol units.

19. The method of claim 18, wherein:
the first layer comprises 3-aminopropyltrimethoxysilane and an amino group;
the second layer comprises an amino-reactive group, a polyethylene glycol chain, and a thiol-reactive group; and
the third layer comprises a thiol group.

* * * * *

UNITED STATES PATENT AND TRADEMARK OFFICE
CERTIFICATE OF CORRECTION

| | | |
|---|---|---|
| PATENT NO. | : 12,090,514 B2 | Page 1 of 1 |
| APPLICATION NO. | : 18/096769 | |
| DATED | : September 17, 2024 | |
| INVENTOR(S) | : Brandon McNaughton et al. | |

It is certified that error appears in the above-identified patent and that said Letters Patent is hereby corrected as shown below:

In the Claims

Column 23, Line 7, In Claim 5, delete "set of set of" and insert --set of-- therefor Column 24, Line 22, In Claim 16, delete "set of set of" and insert --set of-- therefor Signed and Sealed this
Twenty-ninth Day of October, 2024

*Katherine Kelly Vidal*

Katherine Kelly Vidal
*Director of the United States Patent and Trademark Office*